(12) United States Patent
Stetten et al.

(10) Patent No.: US 8,211,020 B2
(45) Date of Patent: *Jul. 3, 2012

(54) COMBINING TOMOGRAPHIC IMAGES IN SITU WITH DIRECT VISION IN STERILE ENVIRONMENTS

(75) Inventors: George DeWitt Stetten, Pittsburgh, PA (US); William David Weiser, Coraopolis, PA (US); David C. Wang, Pittsburgh, PA (US); John M. Galeotti, Pittsburgh, PA (US); Damion M. Shelton, Pittsburgh, PA (US)

(73) Assignee: University of Pittsburgh—Of The Commonwealth System of Higher Education, Pittsburgh, PA (US)

( * ) Notice: Subject to any disclaimer, the term of this patent is extended or adjusted under 35 U.S.C. 154(b) by 221 days.

This patent is subject to a terminal disclaimer.

(21) Appl. No.: 12/039,518

(22) Filed: Feb. 28, 2008

(65) Prior Publication Data

US 2008/0218743 A1 Sep. 11, 2008

Related U.S. Application Data

(63) Continuation-in-part of application No. 10/126,453, filed on Apr. 19, 2002, now Pat. No. 7,559,895, which is a continuation-in-part of application No. 09/686,677, filed on Oct. 11, 2000, now Pat. No. 6,599,247.

(60) Provisional application No. 60/893,047, filed on Mar. 5, 2007.

(51) Int. Cl.
*A61B 8/00* (2006.01)

(52) U.S. Cl. ...................................... 600/443

(58) Field of Classification Search .................. 600/407, 600/424, 425, 427, 443, 444; 128/916
See application file for complete search history.

(56) References Cited

U.S. PATENT DOCUMENTS

| 4,058,001 A | 11/1977 | Waxman |
| 4,200,885 A | 4/1980 | Hofstein |
| 4,381,787 A | 5/1983 | Hottinger |
| 4,444,197 A | 4/1984 | Koyano et al. |
| 4,509,524 A | 4/1985 | Miwa |

(Continued)

FOREIGN PATENT DOCUMENTS

WO   WO 96/36897   11/1996

OTHER PUBLICATIONS

O'Toole R. et al., "Image Overlay for Surgical Enhancement and Telemedicine", Interactive Technology and the New Paradigm for Healthcare, Jan. 19, 1995, pp. 271-273.

(Continued)

*Primary Examiner* — Michael Rozanski
(74) *Attorney, Agent, or Firm* — Reed Smith LLP

(57) ABSTRACT

A device for combining tomographic images with human vision using a half-silvered mirror to merge the visual outer surface of an object (or a robotic mock effector) with a simultaneous reflection of a tomographic image from the interior of the object. The device maybe used with various types of image modalities including ultrasound, CT, and MRI. The image capture device and the display may be enclosed in a sterile container (e.g., a probe bag) and a mirror and mirror housing may be separately attachable to the image capture device and display. In these embodiments, the mirror may be disposable and the sterility of the overall imaging device is maintained.

10 Claims, 17 Drawing Sheets

U.S. PATENT DOCUMENTS

| | | | |
|---|---|---|---|
| 4,624,143 | A | 11/1986 | Green |
| 4,862,892 | A | 9/1989 | Green |
| 5,224,481 | A | 7/1993 | Ishihara et al. |
| 5,230,338 | A | 7/1993 | Allen et al. |
| 5,261,404 | A | 11/1993 | Mick et al. |
| 5,325,859 | A | 7/1994 | Ishihara et al. |
| 5,335,260 | A | 8/1994 | Arnold |
| 5,526,812 | A | 6/1996 | Dumoulin et al. |
| 5,801,312 | A | 9/1998 | Lorraine et al. |
| 5,823,958 | A | 10/1998 | Truppe |
| 5,896,226 | A | 4/1999 | Peuchot et al. |
| 5,898,503 | A | 4/1999 | Keller et al. |
| 5,899,861 | A | 5/1999 | Friemel et al. |
| 5,911,691 | A | 6/1999 | Mochizuki et al. |
| 6,178,340 | B1 | 1/2001 | Svetliza |
| 6,210,331 | B1 | 4/2001 | Raz |
| 6,216,029 | B1 | 4/2001 | Paltieli |
| 6,416,476 | B1 | 7/2002 | Ogasawara et al. |
| 6,447,451 | B1 | 9/2002 | Wing et al. |
| 6,490,477 | B1 | 12/2002 | Zylka et al. |
| 6,599,247 | B1 | 7/2003 | Stetten |
| 7,559,895 | B2 * | 7/2009 | Stetten et al. ............... 600/443 |
| 2002/0120424 | A1 | 8/2002 | Hauger et al. |
| 2005/0101868 | A1 | 5/2005 | Ridley et al. |
| 2006/0257009 | A1 | 11/2006 | Wang et al. |
| 2008/0218588 | A1 * | 9/2008 | Stetten ............................ 348/47 |

OTHER PUBLICATIONS

Hill J, et al., "Telepresence Technology in Medicine: Principles and Applications", Proceedings of the IEEE, New York, US, vol. 86, No. 3, Mar. 1, 1998, pp. 569-580.

Masamune, et al., "*Three-Dimensional Slice Image Overlay System with Accurate Depth Perception for Surgery,*" Conference on Medical Image Computing and Computer-Assisted Intervention (MICCAI), 2000, Lecture Notes in Computer Science, Springer, Berlin, 1935:395-402.

Masamune, et al., "*Study on Three-Dimensional Surgical Support Display Using Enhanced Reality,*"Proc. of 6$^{th}$ Annual Meeting of Japan Society of Computer Aided Surgery, Oct. 1997, pp. 113-114, Tokyo Denki University, Japan.

Nakajima, et al., "*Surgical Navigation System with Intuitive Three-Dimensional Display,*", MICCAI 2000, pp. 403-411, Department of Orthopaedic Surgery, The University of Tokyo, Japan.

Mitschke, et al., "*Interventions Under Video-Augmented X-ray Guidance: Application to Needle Placement,*" MICCAI 2000, pp. 858-868, Siemens AG Medical Engineering, Henkestr, Erlangen, Germany.

Blackwell, et al., "*Augmented Reality and Its Future in Orthopaedics,*" Clinical Orthopaedic and Related Research, 1998, 354:111-122.

DiGioia, et al., "*Computer-Aided Surgery,*" Cybersurgery, 1998, pp. 121-139, Wiley-Liss, Inc.

Fuchs, et al., "*Towards Performing Ultrasound-Guided Needle Biopsies from within a Head-Mounted Display,*" Visualization in Biomedical Computing, 1996, pp. 591-600, Hamburg, Germany.

Fuchs, et al., "*Augmented Reality Visualization for Laporoscopic Surgery,*" MICCAI, 1998, Springer, Berlin, 1996:934-943.

Azuma, R., "*A Survey of Augmented Reality,*" A Survey of Augmented Reality in Presence: Teleoperators and Virtual Environments, 1997, 6(4):355-385.

Fry, et al., "*Ultrasound-Guided Central Venous Access,*" Archives of Surgery, 1999, 134(7):738-741.

Holm, et al., "*Interventional Ultrasound,*" Ultrasound Med. Biol. 1996, 22(7):773-789.

Cardinal, et al., "*Interventional Procedures in Musculoskeletal Radiology—Interventional Techniques: Ultrasound-Guided Interventional Procedures in the Musculoskeletal System,*" Radiologic Clinics of North America, 1998, 36(3):597-604.

State, et al., *Technologies for Augmented Reality Systems: Realizing Ultrasound-Guided Needle Biopsies*, ACM SIGGRAPH, 1996, New Orleans, LA.

Sheafor, et al., "*Abdominal Percutaneous Interventional Procedures: Comparison of CT and US Guidance,*" 1998, 207(3):705-710, Department of Radiology, Duke University Medical Center.

Fisher, et al., "*Small Lymph Nodes of the Abdomen, Pelvis, and Retroperitoneum: Usefulness of Sonographically Guided Biopsy,*" Radiology, 1997, pp. 185-190.

Dodd, III, et al., "*Sonography: The Undiscovered Jewel of Interventional Radiology,*" Radiographics, 1996, pp. 1271-1288.

Liu J., et al., "*The Reliability of Ultrasound-Guided Core Needle Biopsy (US CNB) in the Evaluation of Non-Palpable Solid Breast Lesions,*" Laboratory Investigation, 1999.

Gupta, et al., "*Sonographically Guided Fine Needle Aspiration Biopsy of Abdominal Lymph Nodes: Experience in 102 Patients,*" J. Ultrasound Med., 1999, 18(2):135-139.

Boland, et al., "*Efficacy of Sonographically Guided Biopsy of Thyroid Masses and Cervical Lymph Nodes,*" AJR Am J. Roentgenol, 1993, 161(5):1053-1056.

Memel, et al., "*Efficacy of Sonography as a Guidance Technique for Biopsy of Abdominal, Pelvic and Retroperitoneal Lymph Nodes,*" AJR Am. J. Roentgenol, 1996, 167(4):957-962

C. Lenay, et al., Technology and Perception: the Contribution of Sensory Substitution Systems, IEEE, 1997, pp. 44-53, Universite de Technologie de Compiegne, BP 649-60206 Compiegne, France.

* cited by examiner

COMBINING TOMOGRAPHIC IMAGES IN SITU WITH DIRECT VISION IN STERILE ENVIRONMENTS

RELATED APPLICATION

This application claims the benefit of U.S. provisional application No. 60/893,047 filed Mar. 5, 2007 and is a continuation-in-part of U.S. application Ser. No. 10/126,453 filed on Apr. 19, 2002 (now U.S. Pat. No. 7,559,895, issued Jul. 14, 2009) which is a continuation-in-part of U.S. application Ser. No. 09/686,677 filed Oct. 11, 2000 (now U.S. Pat. No. 6,599,247, issued Jul. 29, 2003).

CROSS-REFERENCE TO RELATED APPLICATION

This application claims the benefit under 35 U.S.C. §119 (e) of the earlier filing date of U.S. Provisional Application Ser. No. 60/893,047 filed on Mar. 5, 2007 and 35 U.S.C. §120 of the earlier filing date of U.S. application Ser. No. 10/126,453 filed on Apr. 19, 2002, which is now patented, as a continuation-in-part, which in turn claimed priority under 35 U.S.C. §119(e) to U.S. Provisional Application Ser. No. 60/216,860 filed Jul. 7, 2000 and under 35 U.S.C. §120 as a continuation-in-part of U.S. application Ser. No. 09/686,677 filed Oct. 11, 2000, which is now patented, which in turn claimed priority to provisional patent application No. 60/216,860 filed Jul. 7, 2000.

BACKGROUND OF THE INVENTION

1. Field of the Invention

The present invention generally relates to image display devices and methods therefor, and, more particularly, the present invention relates to methods and devices for combining a reflection of a tomographic image with human vision during subcutaneous medical procedures using sterile components.

2. Description of the Background

Because human vision depends at least partially on the detection of reflected visible light, humans cannot "see" into objects through which light does not pass. In other words, humans cannot see into the interior sections of a non-transparent, solid object. Quite often, and in many different technology areas, this sight limitation may impede or hinder the effective completion of a particular task. Various partial solutions to this problem have been utilized in the past (miniature cameras, x-ray methodologies, etc.). However, there is a continued need for improvement to the methods by which the interior of an object is displayed, especially using a real-time imaging modality.

Perhaps in no other field is this sight limitation more of a hindrance than in the medical field. Clinical medicine often calls for invasive procedures that commence at the patient's skin and proceed inward to significant depths within the body. For example, biopsy needles introduced through the abdominal wall to take samples of liver tissue for diagnosis of cancer must pass through many centimeters of intervening tissue. One potential problem with such procedures is the lack of real-time visual feedback in the vicinity of critical structures such as the hepatic arteries.

Standard imaging modalities such as Computerized Tomography (CT) and Magnetic Resonance Imaging (MRI) can provide data for stereotactic registration of biopsy needles within targets in the liver, lungs, or elsewhere, but these methods are typically characterized by the physical displacement of the patient between the time of image acquisition and the invasive procedure. Real-time imaging modalities offer more immediate feedback. Among such real-time modalities, ultrasound may be well-suited for guidance of needles because it preferably is relatively portable, is inexpensive, produces no ionizing radiation, and displays a tomographical slice, as opposed to angiography, which displays a projection. Compared with angiography, ultrasound may offer the additional advantage that clinicians are not rushed through procedures by a desire to keep exposure times to a minimum.

Conventional two dimensional (2D) ultrasound is routinely used to guide liver biopsies, with the needle held in a "guide" attached to a transducer. The guide keeps the biopsy needle in the plane of the image while the tip of the needle is directed to targets within that same plane. This system typically requires a clinician to look away from his hands at a video monitor, resulting in a loss of direct hand-eye coordination. Although the clinician can learn this less direct form of coordination, the natural instinct and experience of seeing one's hands before one's eyes is preferred.

As a further disadvantage, the needle-guide system constrains the biopsy needle to lie in the image plane, whereas the clinician may prefer the needle to intersect the image plane during some invasive procedures. For example, when inserting an intravenous (IV) catheter into an artery, the optimal configuration may be to use the ultrasound image to visualize the artery in cross-section while inserting the needle roughly perpendicular to the image into the lumen of the artery. The prior art system just described may not be capable of accomplishing this task.

A related visualization technology has been developed where three dimensional (3D) graphical renderings of previously obtained CT data are merged with an observer's view of the patient using a partial or semi-transparent mirror, also known as a "half-silvered" mirror. A partial mirror is characterized by a surface that is capable of both reflecting some incident light as well as allowing some light to pass through the mirror. Through the use of a partial mirror (or other partially reflective surface) a viewer may see an object behind the partial mirror at the same time that the viewer sees the image of a second object reflected on the surface of the mirror. The partial mirror-based CT "Image Overlay" system requires independent determination of location for both patient and observer using external 6-degree-of-freedom tracking devices, so as to allow appropriate images to be rendered from pre-acquired CT data.

Another recently developed imaging technology merges ultrasound images and human vision by means of a Head-Mounted Display (HMD) worn by the human operator. The location and orientation of the HMD is continuously determined relative to an ultrasound transducer, using 6-degree-of-freedom tracking devices, and appropriate perspectives of the ultrasound images generated for the HMD using a graphics computer.

These prior art systems may not be appropriate for use with a practical real-time imaging device. Controlling the multiple degrees of freedom can be difficult, and the systems may have too many complex parts to be useful. As such, there is recognized a need in the art to provide a device capable of merging a human's normal vision of an object with an "internal" image of the object that emphasizes freedom of operator movement and/or simplicity of design.

SUMMARY OF THE INVENTION

The present invention contemplates, in at least one preferred embodiment, a device and method for merging human vision of the outside of a target object and a reflected tomographic image of the internal features of the same object. The invention may include an image capture device (e.g., a tomographic scanning device such as an ultrasound transducer), an image display device (e.g., a computer or video monitor), and a half-silvered mirror to "fuse" or superimpose the two images together.

In at least one preferred embodiment, the present invention provides a 2D ultrasound transducer, an image display, and a partially reflective, partially transparent, surface (e.g., half-silvered mirror) generally displaced between a target object and the image display. The transducer, the display, and the mirror may be fixedly attached to each other, or one or more elements may be partially or completely moveable with respect to the others. The movement may be accomplished through direct manipulation by the operator or with the use of one or more robotic arms.

In at least one preferred embodiment, the present invention provides a 3D ultrasound transducer, an image display, and a partially reflective surface broadly displaced between a target object and the image display. The image display may preferably display an appropriate slice of the 3D ultrasound data (effectively a 2D tomographic image) to enable a proper combined image to be seen when an observer looks at the target object through the partially reflective surface.

In at least one preferred embodiment, the present invention includes a series of gears, pulleys, or other motion transfer devices installed between the transducer, the display and the half-silvered mirror to allow the angle between the mirror and display to follow the angle between the transducer and the mirror as the transducer is moved. The present invention also contemplates various embodiments where the transducer is free to move in any direction or where robotic systems allow for the remote performance of procedures.

The present invention also includes sterile embodiments of an imaging device that can be used for procedures that require sterility. For example, the half-silvered mirror assembly may be separated from the image capture device and the display such that the image capture device and display may be sterilized according to common practices (e.g., using a conventional probe bag). The mirror and an attached housing are preferably adapted to be "snapped" into place on the display housing such that the image orientations of the present invention are maintained. The mirror and mirror housing may be separately sterilized or may be disposable, with a new mirror/housing being used for subsequent procedures.

These and other details, objects, and advantages of the present invention will be more readily apparent from the following description of the presently preferred embodiments.

BRIEF DESCRIPTION OF THE DRAWINGS

For the present invention to be clearly understood and readily practiced, the present invention will be described in conjunction with the following figures, wherein like reference characters designate the same or similar elements, which figures are incorporated into and constitute a part of the specification, wherein.

DETAILED DESCRIPTION OF THE INVENTION

It is to be understood that the figures and descriptions of the present invention have been simplified to illustrate elements that are relevant for a clear understanding of the invention, while eliminating, for purposes of clarity, other elements that may be well known. The detailed description will be provided hereinbelow with reference to the attached drawings.

The invention contemplates, in at least one presently preferred embodiment, a method and device for merging or superimposing the reflection of a two dimensional tomographic image of the interior of a target object with the normal human vision view of the outside of that same target object. This methodology may be used in any application where viewing the interior of an object is desired, and the methodology is not limited to any particular industry or application. The interior image is preferably captured by any real-time imaging modality, where real-time does not necessarily indicate near-instantaneous display, but only that the target object has not moved significantly since the scanning was performed. One such real-time imaging modality is ultrasound.

Although this methodology and device can be used across many different fields of endeavor, the present invention may find particular applicability in the medical field. Because unwarranted or excessive intrusion into the interior portions of a human body may cause damage, infection, or other unwanted effects, these intrusions should be limited in both the number of instances and the scope of the intrusion. As such, it is preferable to perform subcutaneous procedures with at least some direct sighting of the interior of the patient. Because the medical device applications may be particularly useful, the present invention will be described with reference to such a medical device, but this exemplary disclosure should not limit the scope of the present invention/" to any particular industry or use.

Figure 1:
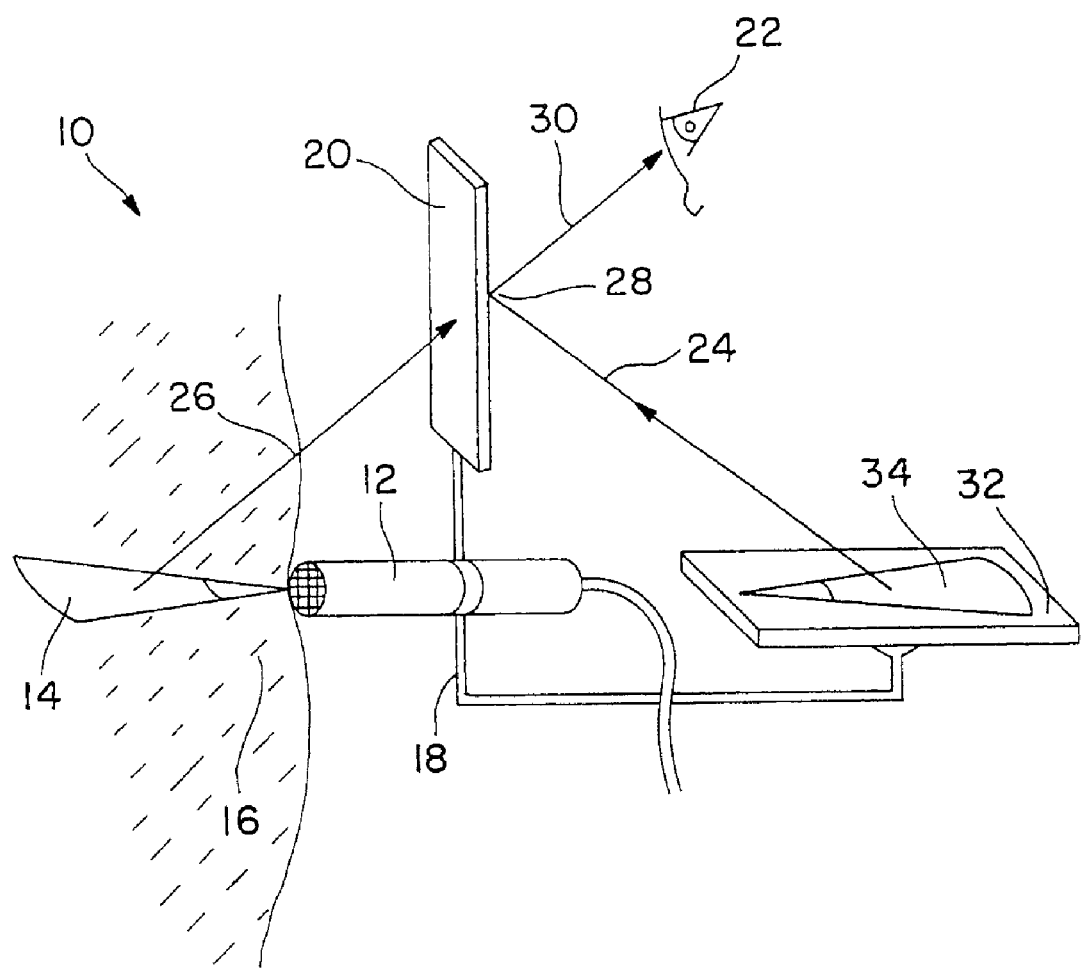
FIG. 1 is a schematic view of a device capable of merging a reflected tomographic image from a 2D ultrasound scanner with a direct view of a target image.

FIG. 1 shows an isometric view of a presently preferred embodiment of an imaging device 10 utilizing a two dimensional (2D) ultrasound transducer 12 capable of taking a B-Mode image slice 14 of a target object 16. In FIG. 1, there is a two dimensional ultrasound transducer 12 fixedly attached to a rigid frame 18. This transducer 12 is preferably a conventional ultrasound transducer that captures a "sonic" tomographic image slice 14 of the interior portion of the target object 16 (in this case a human patient).

Extending vertically from the middle region of the rigid frame 18 is a half-silvered mirror or other semi-transparent, semi-reflective, material 20. The half-silvered mirror 20 allows a user 22 (e.g., a doctor) to look through the mirror 20 at a target object 16 (e.g., a patient) located on the other side of the mirror 20 at the same time that a second image 24 is reflected on the front surface of the mirror (at 28). In this way, the direct target object image 26 and the reflected tomographic image 24 can be combined (image line 30) in the field of view of the user 22.

In FIG. 1, the half-silvered mirror 20 is depicted extending vertically up from the ultrasound transducer 12 midway along the transducer handle, but, in fact, the mirror 20 may be located at some other position in another vertical plane either behind or in front of the depicted vertical plane. More specifically, the FIG. 1 half-silvered mirror 20 could be translated forward or backward (or even tilted) as long as the display 32 is moved in a way that corresponds appropriately (as described in detail below).

At the opposite end of the rigid frame 18 from the transducer 12 is a flat panel display 32 showing the ultrasound image or other tomographic slice 34, with the image portion 34 facing upwards. This display 32 may be any low profile or flat display and may preferably be a liquid crystal display (LCD). When a user 22 looks at a target object 16 through the half-silvered mirror 20, the ultrasound display image 34 will be reflected along line 24 onto the front face of the half-silvered mirror (at 28). The user's sight line 30 will therefore be a combination or superimposition of the direct target object image 26 and the reflection of the ultrasound image 24.

In order to correctly visually merge the reflected ultrasound image 24 with the target object image 26, the ultrasound display image 34 may be reversed (along a horizontal plane), flipped (along a vertical plane), rotated, translated, and/or scaled (depending on the original image 34 location, orientation, and scale on the display 32) so that the reflected ultrasound image 24 on the face of the half-silvered mirror (at 28) correctly portrays the size, scale, and orientation of the ultrasound slice 14 being taken. In a practical sense, if one merely rotates the transducer 12 180 degrees, the ultrasound display image 34 will be flipped exactly as if this image manipulation was accomplished electronically.

A profile of a human operator's eye 22 is shown in FIG. 1 looking through the half-silvered mirror 20 at the target object 16 (patient). Because of well-known laws of light reflection, the ultrasound image 34 on the flat-panel display 32 will be reflected on the operator-side surface of the half-silvered mirror (at 28). Therefore, as the operator 22 looks at the target object 16 through the half-silvered mirror 20, the reflected ultrasound image 24 is merged (superimposed) with or onto the direct target object image 26. To the operator 22, these two images 24, 26 will effectively combine into one image 30 that includes the surface (normal vision 26) of the target object 16 and the interior (reflected ultrasound 24 or other tomographic reflection) of the target object 16. Because the angle of reflection of the ultrasound image follows the operator's sight angle as the operator's head moves, the merger 30 of these two images 24, 26 is independent of the location of the operator 22 (user). Therefore, the user 22 can move his head as well as take full advantage of stereoscopic vision to extrapolate the hidden parts of the invasive tool (e.g., needle) from the exposed parts of the same tool with respect to the anatomical structures in the ultrasound scan.

Because the direct target object image 26 and the reflected ultrasound image 24 are combined or superimposed on the surface of a half-silvered mirror (at 28) that may be naturally within the operator's direct line of sight (along 30), the operator 22 can preferably maintain direct hand-eye coordination throughout the procedure. This natural line-of-sight image combination 30 effectively allows the operator 22 to see "through" the surface (e.g., skin) of the target object 16 and into the underlying structures or layers of materials.

Further, although the present imaging device 10 may be used with virtually any imaging technology, using a nearly instantaneous imaging technology, such as ultrasound, allows the interior and exterior views of the target object 16 to be nearly synchronous. However, the method may be applied to any real-time tomographic imaging modality, where "real-time" refers to any imaging modality that can update the displayed image 34 before the patient (target object 16) moves. As patient movement decreases, "slower" modalities become more useful. If a slower imaging technology is used (i.e., there is a substantial lag time between image capture and image display), the operator 22 may instruct the patient 16 to lie still so that the delayed interior image 34 will remain aligned with the current target object image 26. In this way, even a slower imaging technology may be used with the present invention.

Some possible "quick" imaging modalities include ultrasound, cine-CT and rapid MRI. Some "slower" modalities include conventional MRI, conventional CT, SPECT and PET. However, even these slow modalities may create an accurate combined image 30 so long as the target object 16 has not moved since the last image was captured. A needle or other intruding device may still be introduced using the overlaid image for guidance, provided the target object 16 has not moved. To increase the likelihood that the patient remains still, some combination of laser or ultrasonic range-finders, video cameras, and/or motion sensors (not shown) may be used to detect such movement and warn the operator 22 that the image will not be superimposed perfectly (at 28). Alternatively, these same sensor devices could detect exactly how far the target object 16 has moved since the last image capture and electronically correct the displayed image 34 and/or the location of the display 32 or mirror 20 (see below) to compensate for such target object movement.

Figure 2:
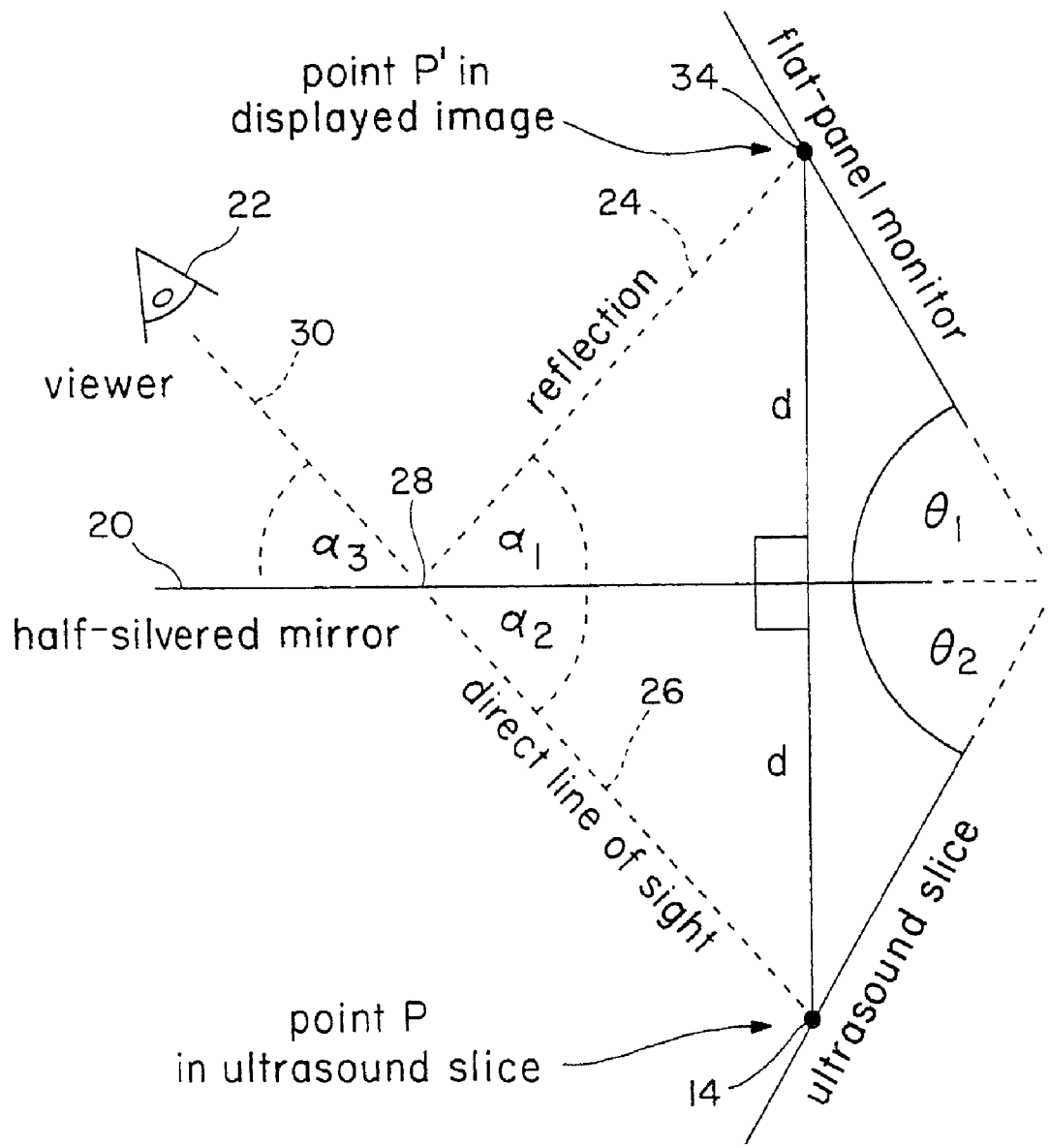
FIG. 2 is a schematic of the image angles that allow the operator to move in relation to the half-silvered mirror while maintaining image merger.
Figure 3:
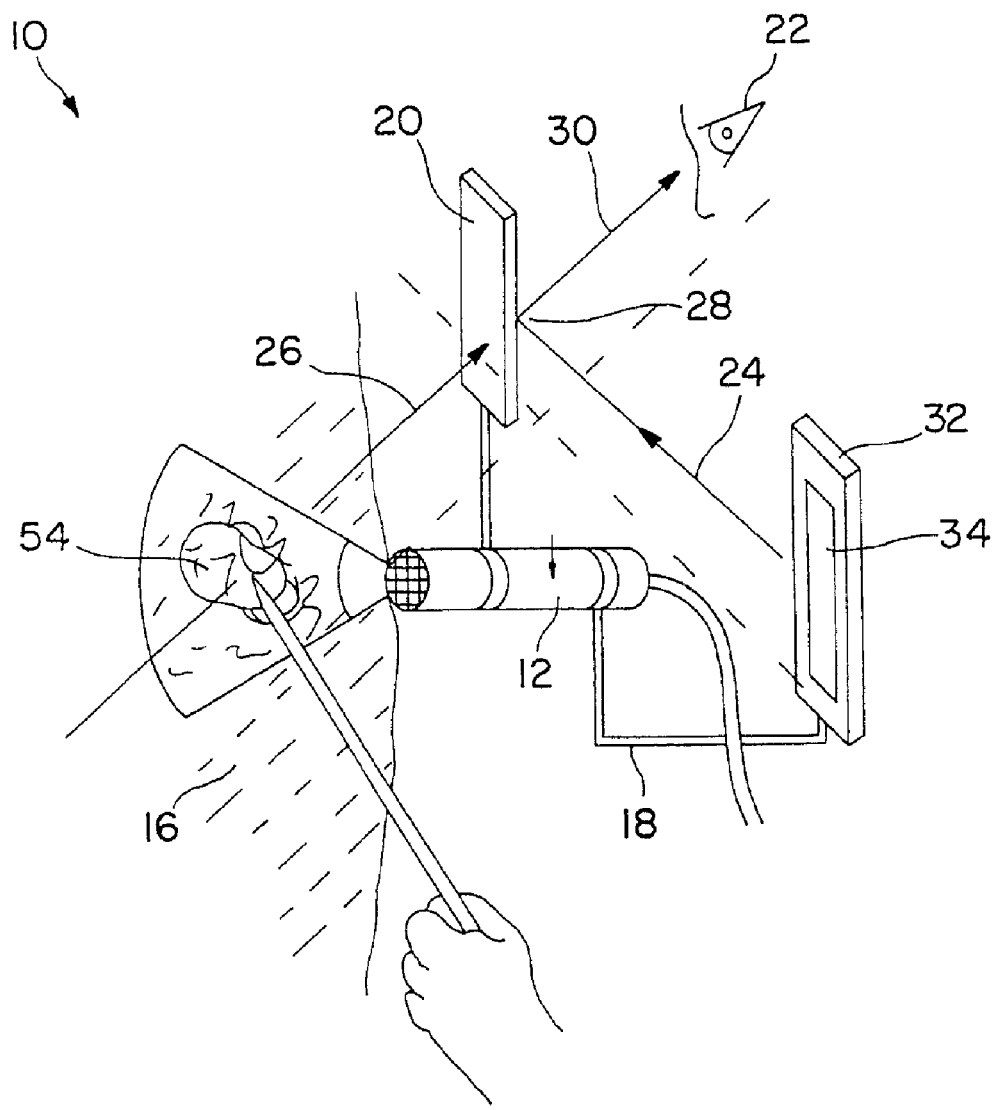
FIG. 3 is a schematic view of a device capable of merging a slice from a 3D scan with a direct view of a target image.

The mathematical requirements for locating the components of the apparatus are shown in FIG. 2. The half-silvered mirror 20 is preferably positioned between the tomographic slice 14 and its image 34 reflected on the flat-panel display, separated from each by the same angle $\theta$ ($\theta_1=\theta_2=\theta$). In essence, the half-silvered mirror 20 bisects the angle $2\theta$. As seen in FIG. 3 (below), $\theta$ can approach zero. Because the mirror 20 in FIG. 2 bisects the angle $2\theta$, point P in the ultrasound slice 14 and its corresponding image P' in the flat panel display 34 are both distance d from the half-silvered mirror 20. The line between the point P in the slice 14 and its image P' in the display 34, along which d is measured, is orthogonal to the plane of the semi-transparent mirror 20.

The figure shows the eye of the viewer 22, to whom the ultrasound display will be superimposed (along 30) on the corresponding physical location of the slice irrespective of the viewer's location. The angle of incidence from the flat panel display 34 to the face of the half-silvered mirror (at 28) is labeled $\alpha_1$ in FIG. 2. By well-known laws of light reflection, the angle of reflection $\alpha_3$ is equal to the angle of incidence $\alpha_1$. Because the mirror 20 bisects 20 and further by well-known laws of geometry, the "incidence" angle $\alpha_3$ from the corresponding point 14 in the target object 16 to the back of the half-silvered mirror 20 is also equal ($\alpha_1=\alpha_2=\alpha_3=\alpha$). In this way, regardless of viewer position, the direct target object image 26 and the reflected tomographic slice image 24 will always coincide to combine image 30.

FIG. 3 shows a presently preferred embodiment of the imaging device 10 utilizing a three dimensional (3D) ultrasound transducer 12. As with the 2D transducer described above, the FIG. 3 embodiment details a half-silvered or partial mirror 20 fixedly attached to the transducer 12 and extending vertically upwards therefrom. In this embodiment, the transducer 12 is capable of capturing 3D imaging data of a scanned volume 54 (e.g., a Real Time 3D (RT3D) ultrasound image). The image 34 that is shown on the flat-panel display 32 (and therefore reflected 24 onto the partial mirror 20) is preferably a 2D tomographic slice through the scanned volume 54 in the target object 16 (for example, a "C-Mode" slice, parallel to the face of the transducer 12). This 2D tomographic image 34 may be mathematically computed from the collected 3D imaging data by a computer (not shown). The flat-panel display 32 should be properly located and oriented to precisely reflect 24 onto the half-silvered mirror (at 28) the location of the corresponding tomographic image within the target object 16. Once again, the image 34 on the display 32 is preferably electronically translated, rotated, scaled, and/or flipped to complete proper registration independent of viewer location, as necessary.

Compared to the "Image Overlay" CT-based system using previously obtained data or any other "lagging" imaging scheme, ultrasound or other "real-time" data is preferred so that the present location of the patient (target object) 16 need not be independently established or registered by the imaging device. Whatever is currently in front of the transducer will simply appear superimposed on the operator's visual field at the appropriate location. Furthermore, the present invention preferably displays only a single slice, as opposed to a complete 3D rendering as in the "image overlay" CT system (described above). Therefore, the visual image merger 30 may be made independent of the observer's location simply by placing the ultrasound display 32 where its reflection 24 in the half-silvered mirror 20 superimposes on the direct view 26 of the target object 16. Since the displayed tomographic image 34 is 2D and is reflected precisely on its proper location in the target object 16, the correct combination 30 of these views 24, 26 is independent of viewer 22 location. This may be simpler and more efficient than superimposing 3D renderings.

The devices and methods as described above include rigidly attaching a semi-transparent mirror 20 and flat-panel display 32 to the tomographic scanning device 12 (or other image capture device). This rigid fixation and the associated bulk of the complete device 10 may reduce the ability of the operator 22 to manipulate the scanning device or transducer 12 during a procedure. There are several ways in which the freedom and ability of an operator 22 to manipulate the image capture device 12 may be increased.

For example, a linkage system of levers, weights, pulleys, and/or springs (not shown) could be constructed, while maintaining the rigid relationship between the device components (scanner 12, mirror 20, display 32), to aid in the manipulation of the entire apparatus 10. This linkage system of levers, weights, pulleys, and/or springs may cantilever or otherwise reduce the amount of force necessary to manipulate the apparatus 10. A similar configuration, for example, is often used in hospitals to aid in the manipulation of heavy lights during surgery. These levers, weights, pulleys, and/or springs are preferably attached to the ceiling or to a floor stand.

Alternatively, the operator 22 may obtain greater flexibility to manipulate the transducer 12 through a system of gears and/or actuators that keep the angle ($\theta_1$) between the display 32 and the half-silvered mirror 20 equal to the angle ($\theta_2$) between the transducer 12 and the mirror 20. As the user 22 moves the transducer 12 in various ways, additional gears, actuators, and/or encoders of linear and/or angular motion could accommodate this transducer motion (and corresponding change in $\theta_2$) by providing equivalent motion of the displayed ultrasound image 34 (and corresponding change in $\theta_1$) through physical manipulation of the display screen 32 and/or electronic manipulation of the image 34 displayed on the screen 32. These gears, actuators, and/or image manipulations preferably keep the appropriate angle ($\theta$) and location between the display 32 and the half-silvered mirror 20 so that the user 22 can move the transducer 12 and still see a proper combination image 30 of the target object image 26 and the reflected ultrasound image 24 independent of viewer location. Such a system could be made to accommodate 6 degrees of freedom for the transducer, including 3 rotations and 3 translations. As with the above embodiments, this embodiment preferably entails physical attachment of the transducer 12 to the rest of the apparatus (which may hinder use of the device 10).

Figure 4:
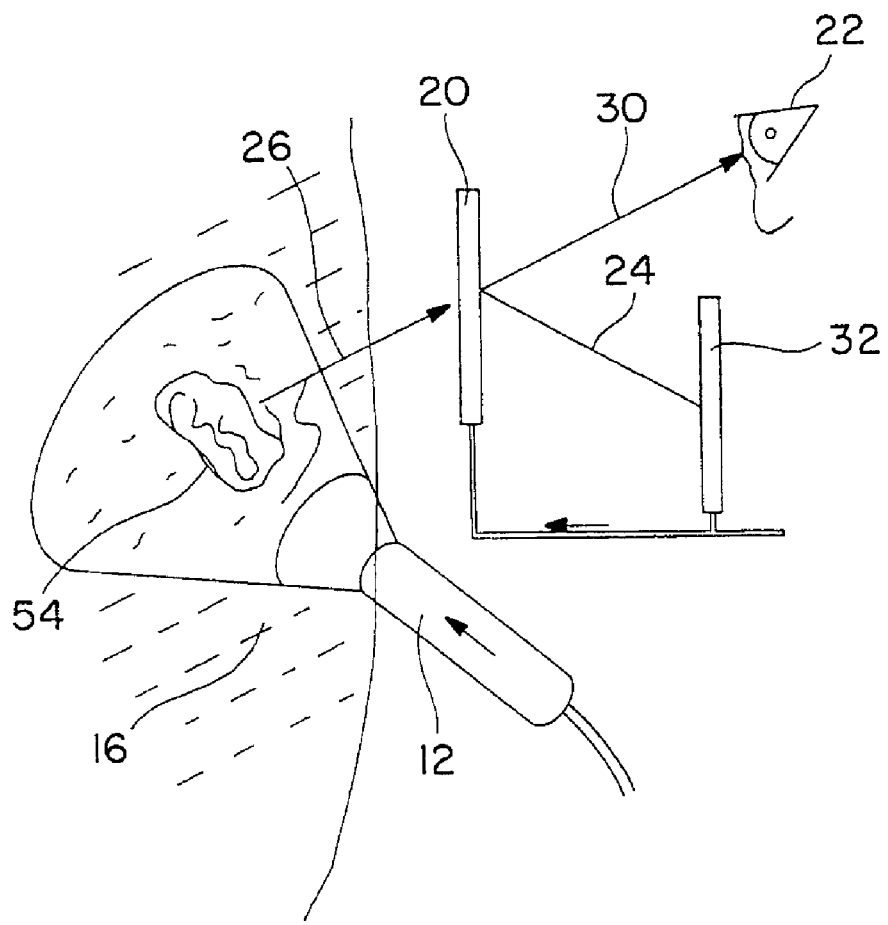
FIG. 4 is a schematic view of an imaging system with the image capture device removed from the remainder of the system.

To further increase the ability of the operator 22 to manipulate the transducer 12 (or other tomographic scanning device), the transducer 12 (or other image acquisition device) may be physically freed from the rest of the apparatus. By continuously determining the relative angles and location of the transducer 12 with respect to the half-silvered mirror 20 using a system such as the commercially available "FLOCK-OF-BIRDS" or "OPTITRACKER" systems, the angle ($\theta_1$) and orientation of the display 32 with respect to the mirror 20 could likewise be adjusted to compensate for this transducer manipulation. One embodiment of a system for freeing a 3D ultrasound transducer 12 is shown in FIG. 4. The appropriate slice through the 3D ultrasound data 54 is computed and displayed (on display 32) so as to effect a merger 30 of the two images 24, 26 on the face of the mirror 20.

Similarly, for 2D ultrasound, the manipulability of the transducer 12 may be especially important when searching for a target. The problem can preferably be addressed by detaching the transducer 12 from the rest of the assembly (the mirror 20 and the flat-panel display 32). A 6-degree of freedom tracking device such as the "FLOCK-OF-BIRDS" or "OPTITRACKING" system may be attached to the handle of the transducer 12. The flat-panel display 32 may be detached from the mirror 20 and controlled by a series of motors such that the display 32 would be made to remain exactly in the reflected plane of the ultrasound slice, as determined by the tracking system on the transducer handle. Such display movement will preferably occur according to well-known principles of robotics.

Such a motorized device may lag behind the movement of the transducer 12 during rapid manipulations of the transducer 12 by the operator 22, but would preferably catch up with the operator at relatively motionless periods when the operator 22 had located a desired target. The mirror 20 may preferably be held motionless relative to the target object 16, establishing the frame of reference for both the transducer tracking system and the motorized display 32. Alternatively, the mirror 20 may be motorized and the display 32 held constant (or both the mirror and the display could move).

The other degrees of freedom which may be necessary to visually fuse 30 (superimpose) the displayed ultrasound image 24 with the actual target image 26 may be supplied by graphical manipulation of the displayed image 34 on the flat-panel display 32, based on the tracking of the transducer 12. As with the fixed and geared assemblies described above, the motorized display 32 and graphical manipulation of the displayed image 34 preferably provides visual "fusion" 30 of the reflected ultrasound image 24 with the actual target object image 26 independent of operator 22 or target object 16 location.

In one presently preferred embodiment of the invention, two robotic arms, or a single paired robotic device, manipulate both the transducer 12 and the display 32 (and/or the mirror 20) under remote control in such a way that the visual fusion 30 is maintained. This may eliminate the need to track the transducer 12, replacing it with feed-forward remote control of the transducer location via a joystick or other controller. The simultaneous control of two robotic devices whose motions may be as simply related as being mirror images of each other, may be accomplished in a fairly straightforward manner, and may exhibit a more synchronous image fusion.

A natural pivot-point for the display monitor may be the reflection of the point of contact between the transducer and the target object because, during many procedures, the operator tends to rotate the ultrasound transducer in all three rotational degrees of freedom around this point (to find a desired target). Thus, for the simultaneous control of two robotic devices just described, rotating the display monitor with three degrees of freedom around this point may be preferred. For systems that move the display while tracking a manually manipulated transducer, at least one translational degree of freedom may be needed to allow the display monitor to become coplanar with the ultrasound slice.

Calibration of the fixed system and development of the servo-linked (motorized) display system or the dual robotic system just described may require careful consideration of the degrees of freedom in the registration process. First, consider only the geometric transformation, i.e., assume the scale of the captured slice and the displayed image are identical and undistorted. To complete the geometric transform registering the reflection of the ultrasound image to the actual slice, we need to satisfy 6 degrees of freedom. First we have 3 degrees of freedom to manipulate the display physically into the plane of the slice reflection. This can take the form of two rotations to make the display screen reflection parallel to the slice and one translation orthogonal to the display screen to bring it into precisely the same plane.

Once the display reflection and the slice are in the same plane, three additional degrees of freedom may be employed to match the image and the slice, which may be achieved through two translations and one rotation of the image on the display. In essence, the 6 degrees of freedom place the display in the proper physical plane to reflect the image on the half-silvered mirror (3 degrees of freedom) and then rotate and translate the image on the display so that the correctly placed reflection is properly aligned (3 additional degrees of freedom) on the mirror with the actual target object image.

Beyond the geometric transformation, further calibration may be required. First, the proper scale must be calibrated. This includes isotropic scale (similarity transform) and non-isotropic scale (affine transform). Further corrections may be required for non-linear geometry in both the imaging system and the display by warping of the image.

To the extent that the geometric properties of the slice do not change with tissue type, and the slice geometry does not change as the transducer is moved relative to the target object, calibration of the system 10 may only need to be performed initially, using a phantom target object (not an actual patient). Such calibration will suffice for slice geometry due only to the scanner. Further changes in image geometry due to tissue properties will depend on transducer location relative to the tissue. These changes may be due to differences in the speed of sound in different tissue types. It may be possible to correct for these using image analysis techniques as known and developed in the art.

A problem with calibration may arise because a phantom in a water tank that is easily scanned using ultrasound will appear displaced to human vision due to refraction at the air-water interface. Several solutions are described here to this problem. One solution may use a rod that intersects both the reflected image (in air) and an ultrasound slice displaced along the rod (water). The display may then be physically moved or rotated, and the image on the display may be electronically moved or rotated, to make the rod appear to intersect the corresponding reflected ultrasound image appropriately.

A second calibration solution includes the use of a calibration phantom. The phantom is placed in water or some other ultrasound transmitting (but light refracting) medium and scanned by the image capture device. The image is "frozen" (i.e., still picture) on the display and reflected off of the half-silvered mirror. Without moving the calibration phantom, the water or other medium is drained or removed from the calibration setup. The user can then adjust the display or the image on the display until the "frozen" reflected scan image of the phantom aligns with the direct sight image of the calibration phantom. Many other calibration schemes could be used within the scope of the present invention.

Figure 5:
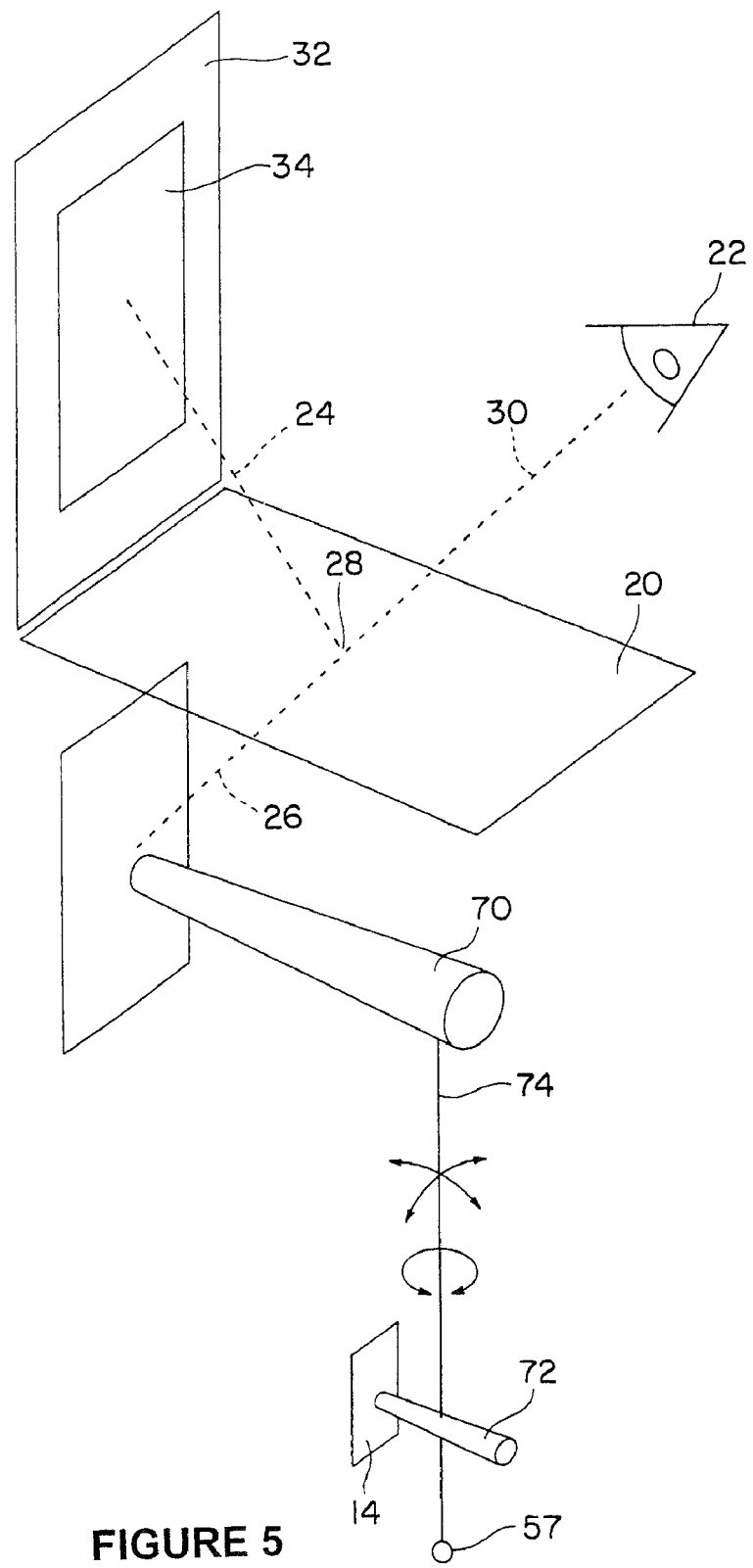
FIG. 5 shows the methodology applied to remote operation using a mock effector in the field of view.
Figure 6:
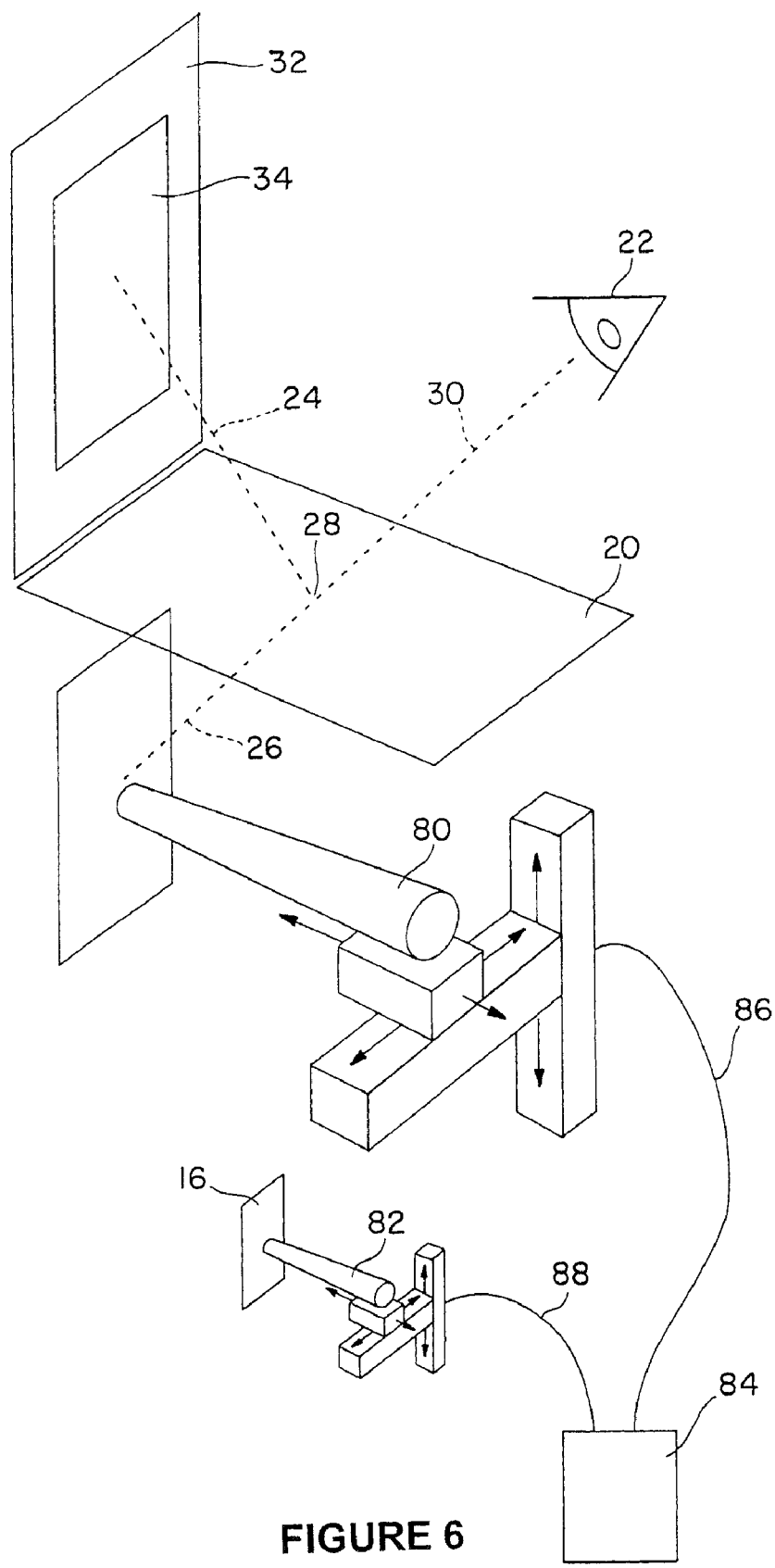
FIG. 6 shows the methodology applied to remote operation utilizing a remote-controlled effector.

In one presently preferred embodiment of the present invention, a "remote" procedure is performed through the use of a tomographic scanning device and surgical implements controlled remotely with a mechanical or robotic "mock effector" in the operator's field of view instead of the actual target object being in the operator's field of view. A mock effector is a physical replica of the actual invasive instrument, preferably of identical shape but not necessarily identical scale. The mock effector may either be directly controlled by the operator (FIG. 5) with mechanical linkages, encoders and/or tracking devices relaying the desired motion to the actual effector, or alternatively the operator may use a remote control to activate both the mock effector and actual (surgical) effector with corresponding motions (FIG. 6).

For example, a procedure may involve using a hypodermic needle or micro-pippette to take samples in a certain plane. In FIG. 5, the tomographic scanning device (not shown) may be aligned to capture a slice 14 of the target object from which the sample may be taken. The action of the actual surgical needle 70 may be controlled remotely by operator 22 manipulation of a mock effector (needle) 70 in the user's field of view demonstrating the precise motion of the actual remote effector 72, although possibly at a different scale. The scale (as well as the location and orientation) of the mock effector 70 would match that of the reflected tomographic image 24 (to make the combined image 30 an accurate representation).

In this example, a mock needle 70 may be present in front of the operator 22 (remote from the target object). The operator 22 preferably looks through the half-silvered mirror 20 at the end of the mock effector 70. The operator's field of vision is a merged image 30 of the direct view 26 of the mock effector and the reflection of the tomographic slice 24. If the actual needle 72 performing the procedure on the patient (target object 16, not shown, through which tomographic slice 14 is acquired) is of a different scale than the mock effector needle 70, then the tomographic image 34 displayed on the monitor 32 is preferably moved and/or scaled so that the reflected tomographic image 24 and the direct view 26 of the mock effector are of equal size, scaling, and orientation at the surface 28 of the half-silvered mirror 20.

The mock effector needle 70 and the actual surgical effector needle 72 are preferably connected through some sort of control mechanism 74. In FIG. 5, this control mechanism is shown as a direct mechanical link 74, being a rod fixed at one end by a ball-and-socket 57 to allow 3 degrees of rotation. As the operator manipulates the mock effector 70, the actual effector 72 will move correspondingly (although on a smaller scale). Similarly, the control mechanism may be some type of tracking or encoder device that registers the movement of the mock effector 70 and transfers this movement to the actual surgical effector 72. In this way, the operator can manipulate a mock effector 70 and cause a procedure to be performed on a target object at a remote location.

This remote procedure model may be useful for extremely small scale procedures. For example, assume a microscopic region of a patient must be cut (e.g., a cancer cell removed or a cornea operated upon). In the region of a very small cutting implement, a specialized tomographic scanning modality (such as Optical Coherence Tomography (OCT) or a high frequency (100 MHz) ultrasound) may be used to capture an image slice. At a remote location, a doctor may preferably look through a partial mirror with a reflection of the tomographic slice on its face superimposed upon a mock cutting implement whose motion is linked to that of the actual cutting implement. Although the actual procedure occurs on a microscopic scale, both the tomographic slice and the mock effector can be magnified or scaled up to a point that allows the doctor to perform the procedure in a more relaxed and accurate manner. As long as the mock effector is scaled up to a similar size as the tomographic slice, the overlay of the images may be accurately located and oriented with respect to each other. In this way, small scale medical (or non-medical) procedures may be easier to perform. Similarly, large scale procedures such as undersea robotics using sonar-based tomographic imaging may be performed remotely at a smaller scale than they actually occur.

FIG. 6 details one possible robotic version of the present invention. The FIG. 6 remote application is generally similar to the FIG. 5 implementation with the addition of a control box 84 used to control the motion of both the mock effector 80 and the actual surgical effector 82. As in the previous example, the operator 22 looks through the surface of the half-silvered mirror 20 at the working end of a mock effector 80. A tomographic image 34 of the target object 16 is displayed on a monitor 32 and reflected along line 24 onto the surface of the half-silvered mirror 28. The operator's field of view includes the merger 30 of these two images 24, 26.

In this example, however, the operator 22 preferably does not directly manipulate the mock effector 80. Instead, some type of control, for example a joystick, keyboard, voice activated software, or other device, is manipulated by the operator 22. This control device causes the movement of both the mock effector 80 (through control line 86) and actual effector 82 (through control line 88). In FIG. 6, each of these effectors 80, 82 can be moved with 3 degree of freedom movement. The mock effector 80 can again be scaled larger or smaller to make the manipulation of the actual effector 82 more convenient. Preferably the size, scale, and orientation of the tomographic image 34 displayed on the monitor 34 is matched to the size, shape, and orientation of the mock effector 80.

For robotic versions of the present invention, the effector 82 that interacts with the patient 16 need not necessarily be a mechanical surgical tool. For example, the effector could be a laser, RF (radio frequency) transmitter, or other device for delivering or imparting energy or matter on a target object. In these cases, the mock effector used by the operator may include some kind of demonstration of the energy or matter delivered, either expected or measured, to the patient. For example, an isosurface of expected RF field strength may be physically constructed and mounted on the mock effector used by the operator such that the field model intersects the reflected image appropriately. In this way, the operator can take into account the field of the effector's use, as well as the effector itself.

The present invention may also depend on the lighting used on or around the device. For example, light that hits the surface of the half-silvered or partial mirror from above (operator-side) may introduce unwanted reflections in the semitransparent mirror. In this case, the target object will be more difficult to see. Alternatively, light that comes from a source beneath the half-silvered mirror (on the same side of the mirror as the target object) may increase the clarity of the target object image without introducing unwanted light reflections onto the half-silvered mirror. Various types of lighting (e.g., visible, ultraviolet) as well as paints, markings, and light emitting markers on the targets or tools themselves may have different properties that are adjustable to change the contrast, intensity, and interpretability of the image superimposition.

Alternative forms of light may also be used to register locations in the ultrasound during a procedure. These alternative light sources can be used to identify certain features of the target object in addition to the 3D visual cues inherent to superimposition of the reflected image. For example, a plane of laser light can be created with a movable mirror and a laser such that any real object (part of target object or mock effector) that intersects the plane of laser light will be "marked" by the colored lines of the laser light. Such a laser marking system could be used with a computer vision system to permit automated detection and location determination of the intersection point of the located object and the light plane. This system may be used for automated calibration with corresponding features detected in the tomographic image.

Light sources could also be arranged relative to opaque shields so that only certain parts of the target object are illuminated, such as all parts beyond (or nearer to) the reflected tomographic image. Thus, the image would fall on what would effectively be a clipping plane through the object, with all parts of the image closer to (or further from) the viewer not illuminated. Sound, tactile, and/or other forms of feedback may be provided to the operator based on the location of tools relative to the reflected image. These feedback indicators may alert the operator when contact is made, for example between the tip of a needle and the reflected slice.

Various techniques may be used to alter the image as viewed on the low-profile display. The image may be rotated, translated, scaled, or distorted, as previously described, or otherwise cropped or manipulated in many ways according to the needs of the user of the system. For example: extraneous parts of the image may be removed; specific anatomical targets may be automatically identified and graphically enhanced; surgical tools may be tracked and their hidden sections graphically simulated; and/or other useful information may be superimposed on the displayed image for the operator relating to the invasive procedure.

In all, the present invention may be useful for many medical procedures including amniocentesis; many forms of surgery; soft tissue biopsy of organs such as liver, kidney, or breast; and procedures such as the insertion of central venous lines, or even peripheral intravenous catheters. In brain surgery, for example, deformation of the brain after removal of portions of the skull leads to inaccuracy of registration in non real-time modalities such as conventional CT. Real-time guidance using ultrasound may compensate for such deformations, as well as provide adaptive guidance during the removal of an abscess, for example, or in other cases where structures may change shape or location during procedures. Another example is monitoring and correction of tissue infiltration during the infusion of cancer drugs into large veins. The invention may positively affect the success and flexibility of these and other invasive procedures.

Since the visual image merger is independent of viewer location, two or more human operators may work together in the same field of view, assisting each other manually and/or offering consultation. The invention may be valuable in teaching, for example, by clarifying the content of ultrasound images through its location in the target object.

As briefly mentioned above, the version of the device using a mock effector could be used at microscopic scales, for example, to insert micro-pippettes into individual cells under OCT guidance to gather intracellular samples to determine whether the cells are of a cancerous nature (or to deliver therapeutic agents to a single cell). Other possible examples include the use of very high frequency ultrasound to guide microscopic surgery on the cornea, and high resolution MRI to guide biopsies of tissue samples of small animals. It may also be used to guide the administration of radiation and other non-invasive procedures, to guide procedures at the end of a catheter or endoscope equipped with a tomographic scanner, or in many other technical and non-technical applications.

One or more of the above embodiments may be oriented toward a portable version of the present invention. The size, shape, and materials used may be minimized so that the entire apparatus can be carried by a single user (or a few users) to the site of a procedure. An ultrasound transducer is preferably used in the portable embodiment because of its small size and ease of use. These embodiments may be especially suited for use in the battlefield for the removal of foreign bodies such as bullets or shrapnel.

Figure 7:
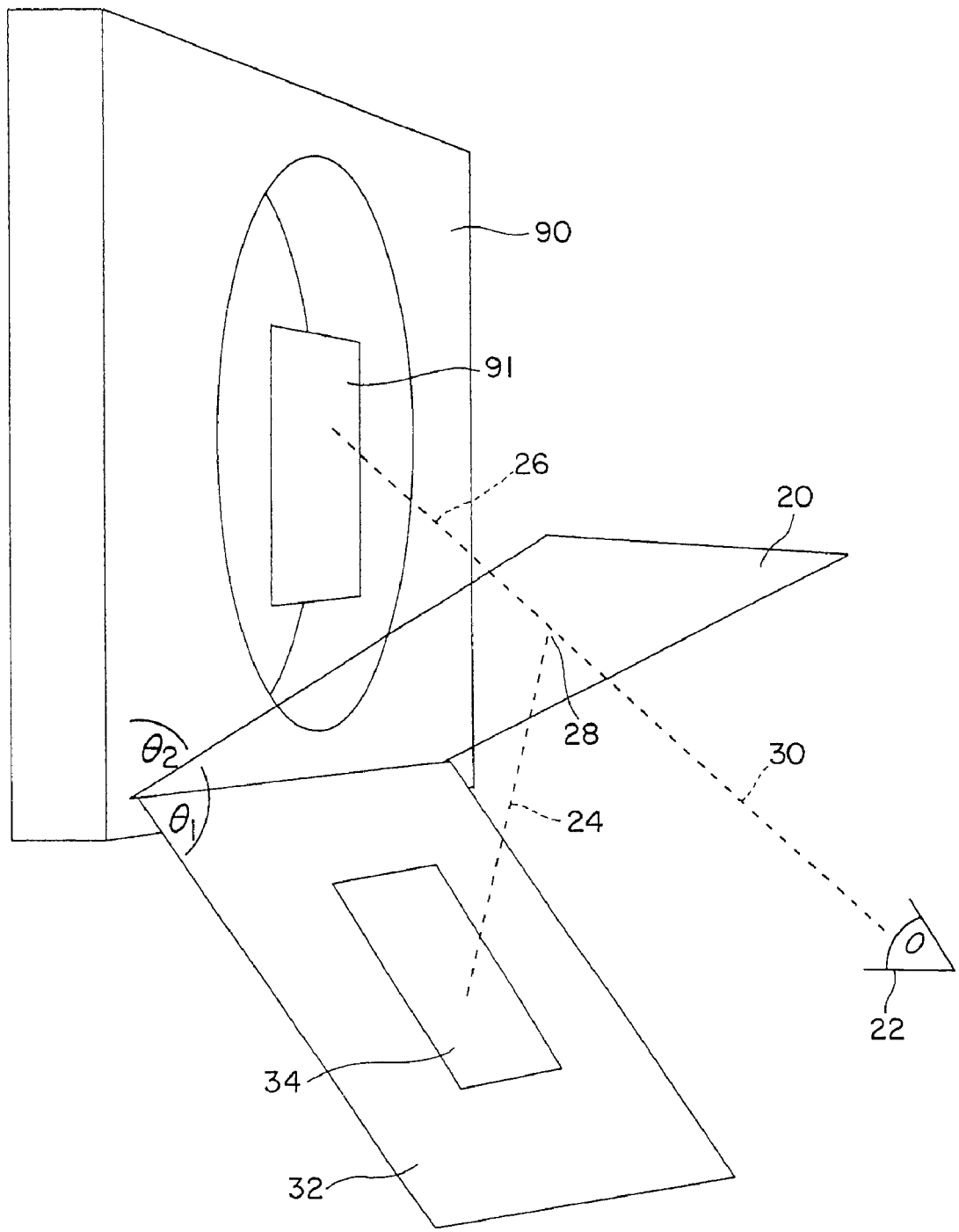
FIG. 7 is a schematic diagram of the present methodology applied to the front of a large imaging machine such as a CT scanner.

The ultrasound transducer in the above portable version may be replaced (towards the opposite end of the size spectrum) with a comparatively massive CT or MRI scanner (see, FIG. 7). The principle of operation is still based on a controlled geometric relationship between the scanner, the mirror 20, and the display 32, just as in the above embodiments. In essence, the angle ($\theta_1$) between the display 32 and the half-silvered mirror 20 should be equal to the angle ($\theta_2$) between the mirror 20 and the slice 91 through the target object within the gantry of the CT or MRI scanner 90.

The image from a CT or MRI machine can often be converted into an appropriate tomographic slice within less than one minute from the image scanning. Once a CT scanner is no longer transmitting X-rays (after the image is captured), there will be no harmful exposure to the operator. As seen in FIG. 7, the gantry 90 of these machines may provide ample access for a doctor or other user 22 to perform an invasive procedure on a patient within the CT machine. Furthermore, if the space in the gantry 90 is not sufficient for a particular procedure, the patient (or other target object) may be moved out of the machine a known distance, and the image 34 of the tomographic scan may then be shifted by that same amount (provided the patient did not move in any other way).

There are many other embodiments and alternatives that may be used in combination with the general structures of the present invention as described above. For example, a jig can be used to "store" the geometric relationships between the image acquisition device (tomographic scanner) and the target object to allow for the use of the invention without the image acquisition device being present upon viewing.

Figure 8A:
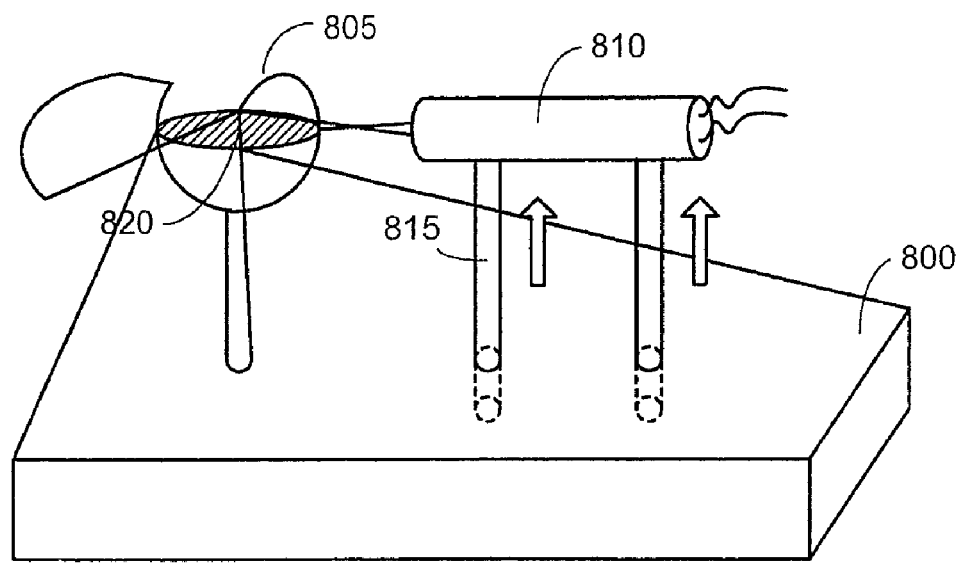
FIG. 8 shows an image acquisition device inserted into a jig (8A) and the jig with the image acquisition device replaced with a screen/mirror apparatus (8B)

FIG. 8A shows one exemplary embodiment of a jig 800 that may be used to store the geometric relationships of the system. The target object 805 and the image acquisition device 810 (in this case an ultrasound transducer) are mounted in a jig 800 using one or more pegs 815. The jig 800 is used to define the spatial relationships between the ultrasound transducer 810 and the target object 805. Once in position, a tomographic slice image 820 of the target object 805 can be obtained and stored for later use.

Figure 8B:
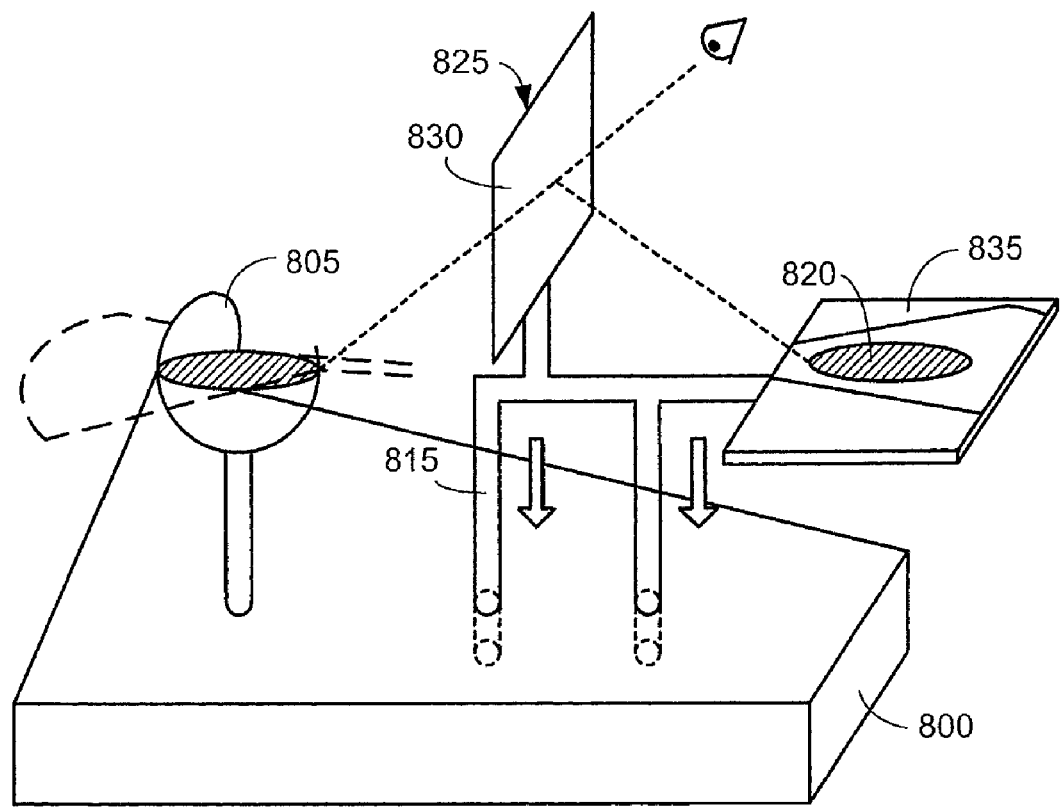

FIG. 8B shows the same jig orientation with the data acquisition device removed. In its place, a display assembly 825 is inserted into the jig 800. In much the same way as previously described embodiments, FIG. 8B shows a half-silvered mirror (partially reflective surface) 830 oriented between the viewer's eye and the target object 805. Further, a flat panel or other display 835 is connected to the jig 800 such that it reflects a captured image onto the user-side face of the half-mirrored surface 830.

If the image capture device 810 from FIG. 8A is used to capture an image 820 of the target object 805, and the flat panel display 835 of FIG. 8B is used to display the captured image 820 at a later time, the reflected view of the interior portion of the target object 805 will be superimposed on the direct view of the target object 805 on the surface of the half-silvered mirror 830. Because the jig 800 keeps the geometric orientations between the target object 805, mirror 830, image acquisition device 810, and display 835 such that the desired relationships described above are satisfied, the jig 800 can be used to make real-time use of the image acquisition device 810 unnecessary for certain applications. The captured tomographic image 820 will not be in real-time, but may still be useful if the target object is kept motionless (or nearly motionless) during a procedure.

As described above, the present invention is preferably calibrated before use to ensure proper orientation of the components and display of the captured image. Specifically, the flat panel display must be oriented with respect to the half-silvered mirror such that the reflected tomographic image is correctly superimposed on the direct view of the target object through the half-silvered mirror. This includes calibrating with both a geometric transform to ensure that the slice and display are coplanar and an affine (or other) transform to scale the ultrasound slice to its correct size, to adjust its aspect ratio, and to correct for skewing. Improved methods for both types of calibration are now given.

Certain computers (e.g., SILICON GRAPHICS O2) are capable of mapping a video image through an affine transform (or other transforms) in real-time. The affine transform permits the tomographic slice displayed on the monitor to be translated, rotated, and anisotropically scaled. The calibration process becomes a matter of finding the optimal parameters for the affine transform.

Mapping location (x,y) to (x',y') with an affine transform is accomplished by multiplying the homogeneous form of (x,y) by a 3×3 matrix A. As shown in equation (1), an affine transform is capable of mapping any triangle to any other triangle. If the mapping for 3 locations is known, the computer can solve for the matrix A. Since matrix A has only six unknown elements, it will have an explicit solution (assuming the 3 locations are not collinear).

$$\begin{vmatrix} x'_1 & x'_2 & x'_3 \\ y'_1 & y'_2 & y'_3 \\ 1 & 1 & 1 \end{vmatrix} = \begin{vmatrix} a_{1,1} & a_{1,2} & a_{1,3} \\ a_{2,1} & a_{2,2} & a_{2,3} \\ 0 & 0 & 1 \end{vmatrix} \begin{vmatrix} x_1 & x_2 & x_3 \\ y_1 & y_2 & y_3 \\ 1 & 1 & 1 \end{vmatrix} \quad (1)$$

Based on this theory, a "bead phantom" may be constructed with three (or more) training beads suspended in roughly an equilateral triangle generally in the plane of the tomographic slice being taken. An uncalibrated tomographic slice image from this phantom (which may be suspended in a water tank) will be captured and displayed on the flat panel display. The water (or other fluid) will then be drained to avoid diffraction errors at the air-water interface during visual inspection. The affine transform may then be found that maps the locations of each of the three training beads in the stored ultrasound image to its corresponding visual location (as seen through the half-silvered mirror). Assuming that the beads in the phantom are actually in the plane of the slice, the calibration process will be independent of viewer location.

Figure 9A:
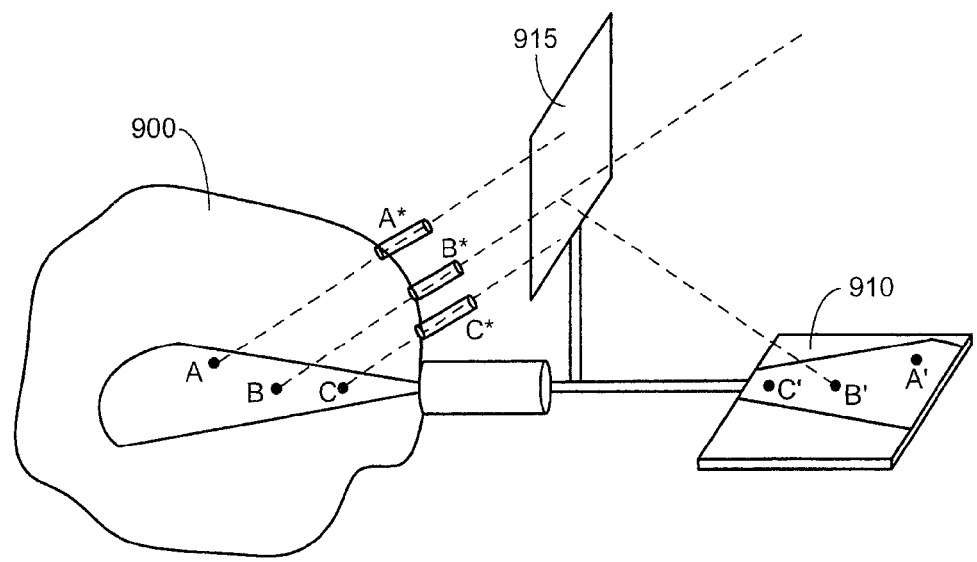
FIG. 9 shows a calibration system for the present invention (9A) with exploded views of tubes attached to the target before (9B) and after (9C) gel is added.
Figure 9B:
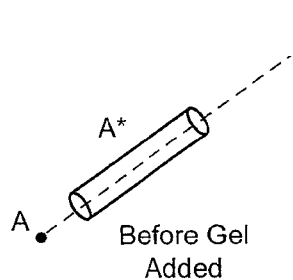

FIG. 9 shows one exemplary embodiment of an improved calibration method for the present invention which may be used to verify the above calibration method. FIG. 9A shows a calibration target object known as a phantom 900. The phantom 900 contains three (or more) targets (A, B, C) inside its surface. In FIG. 9A, the phantom 900 is shown with three beads A, B, C suspended by a thread which is not shown for clarity. The phantom 900 is subsequently filled with a gel or other fluid (to enable tomographic imaging). Three tubes A*, B*, C* are mounted on the exterior surface of the phantom 900 such that each is pointed at its corresponding interior bead (i.e., when looking through the tubes A*, B*, C*, the corresponding target bead A, B, C will be seen). The tubes may be placed after the target beads are in place, or the beads (or other targets) may be inserted using thin rods through the tubes as a guide for insertion (see, FIG. 9B).

Figure 9C:
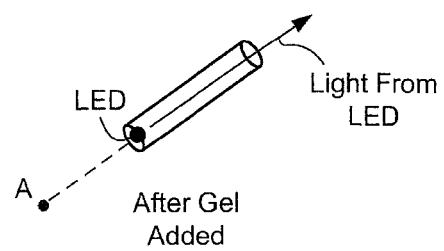

In either case, after the tubes A*, B*, C* and target beads A, B, C are fixed into position, a small LED, light source, or other visual indicator is preferably inserted into the base (phantom side) of each tube A*, B*, C* (see, FIG. 9C). These LEDs can be seen by the viewer looking through the half-silvered mirror when the viewer is looking parallel to the long axis of the tube. After the gel is inserted in the phantom and the LEDs are in place, the viewer can determine that he or she is looking directly at a target bead A, B, C by seeing the corresponding LED through its tube A*, B*, C*.

The slice through the three target beads A, B, C displayed on the flat panel display 910 as A', B', C' is reflected on the face of the half-silvered mirror 915. The corresponding reflections of the displayed images of each target bead A', B', C' can be aligned with the appropriate LED (in direct view) by using three independent (x,y) translations to calculate an affine transform as described above. The co-planarity of the display's reflection and the ultrasound slice will have to be pre-established (through conventional techniques or as described below), and the three target beads will have to be visible in the ultrasound slice. Given all of the above, a virtual target can then be displayed, a needle (or other tool) may be inserted, and the geometric error can then be determined by measuring the intersection of the needle in the ultrasound slice relative to the displayed virtual target (anywhere in the image assuming linearity).

In addition to the affine transform described above, the components of the system must also be geometrically calibrated. Specifically the tomographic slice being captured must be coplanar with the flat panel display being reflected onto the half-silvered mirror in order for the simple geometric relationships of the present invention to be satisfied. The present method replaces an ad hoc "by eye" approach with a method in which targets within the slice and the virtual image are optically determined to be coplanar using a video camera. The method may be undertaken either by the plane of focus of the video camera or by the camera's exhibition of zero parallax when it is moved to a different location.

For the focal plane approach, the water (if any) would be drained from a tank holding the target to permit direct viewing of the target (such as beads on a string). Initially, the target beads and virtual image are viewed through a video camera. The plane of focus of the camera would then be changed in some measurable way. If the target bead were coplanar with the virtual image on the display, the video images of both would go in and out of focus simultaneously. Analysis of the frequency of the spectra of the video image sequence would reveal a single frame with a maximum high frequency. Two such frames, however, would be observed if co-planarity had not been achieved. After adjustments, this geometric calibration confirmation could then be repeated.

An alternate method to ensure co-planarity between the display and the captured slice may be based on parallax. This method preferably aligns targets in the tomographic image with the corresponding features in the virtual image from one point of view, and then moves the video camera to another point of view to verify continued alignment. Errors thus introduced in the alignment could be used to calculate corrections in the position of the flat panel monitor, bringing its virtual image into co-planarity with the ultrasound slice.

The parallax method could be used on the "virtual line of sight" phantom (with tubes containing LED's, FIG. 9) by providing multiple tubes for each target pointing in different directions. For example, a system of three targets with six tubes may be used as an exemplary embodiment, with each set of three tubes converging on a different viewing location. Video cameras at these two locations would capture the required parallax information.

The present invention may also take advantage of methods and apparatuses for the guiding of invasive devices such as guiding the insertion of a needle 1000 during a biopsy procedure. One preferred embodiment, shown in FIG. 10, introduces the use of an oriented light source 1005 to specify a path to an internal target A. For example, in addition to the flat panel display 1010 (or in place of the flat panel display), a tube containing a light source 1015 (or simply a directional light source such as a laser) is positioned on the same side of the mirror as the viewer such that the virtual image of the light 1020 coincides with the desired needle path 1000 within the patient. The combined view of the two image paths is depicted as image line 1025. The intended needle path 1000 may be determined in a number of ways, including the use of image data from a scanner physically attached to the device or otherwise geometrically related to the device by use of a jig if image data was previously acquired.

The laser or other light may also be reflected off of the flat panel display and up to the half-silvered mirror. With this orientation, the light source 1015 would not interfere with the reflection of the displayed tomographic slice, and the user's view 1025 may be less obstructed. An almost limitless configuration of light sources and mirrors could be used to effect this reflection.

Figure 10:
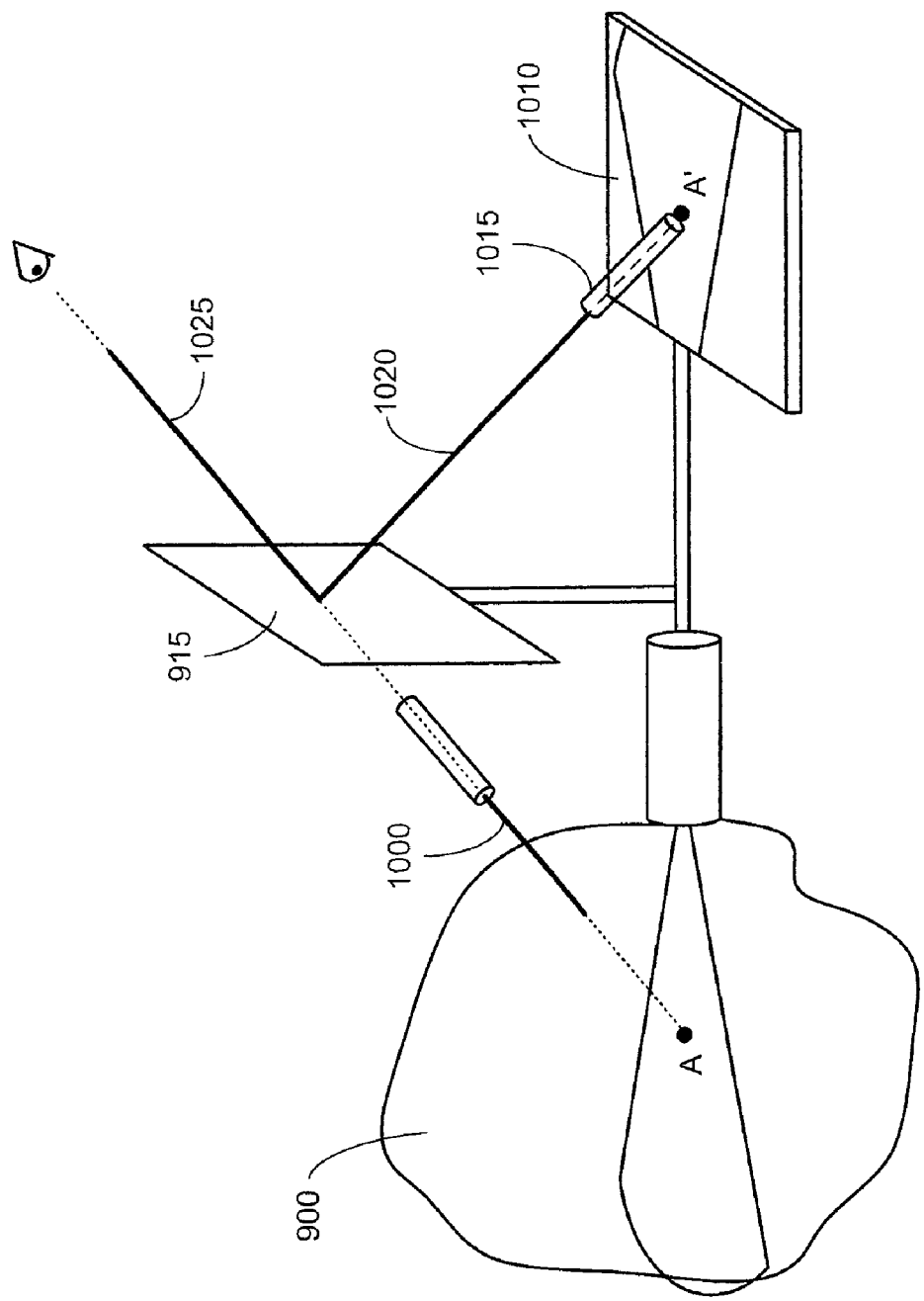
FIG. 10 shows a light source guidance method according to the present invention.

To determine light source placement, human and/or computer analysis of the image data (which may be 3D in the case of CT, MRI, 3D ultrasound, etc.) may be used to initially and/or continually provide a needle path that hits the target while avoiding critical structures such as arteries. Light emanates from the tube such that the operator may find the appropriate entrance location and initial orientation for the needle. During insertion, continual guidance may be intuitively applied by keeping the exposed shaft of the needle aligned with the virtual image of the tube. Marks on the needle shaft can be visually aligned with corresponding marks on the tube to determine depth of insertion and alert the operator when the target has been reached. FIG. 10 shows a 2D version of this embodiment.

The reverse of this "light" system could also be used to guide needles or other tools into the target object. For example, a biopsy needle (or other tool) with small lasers mounted on the back of, and on opposite sides of, the needle which point parallel to the long axis of the needle (down its shaft) may be used. The lasers will be reflected off of the half silvered-mirror and down to the face of the flat panel display (with the half-silvered mirror oriented parallel to the plane of the display and the image capture device). These lasers will appear as two "dots" (or other shapes) on either side of the target on the flat panel display. These marking dots represent the position at which the needle is currently aimed in the target image. By watching the movement of the dots on the face of the display (or in the reflection inside the patient), the needle or other tool may be properly guided into the target image.

One potential drawback of at least one embodiment of the present invention is the angle of refraction that occurs as the various images pass through the glass of the half-silvered mirror. Because the reflected image bounces off the face of the mirror and the direct view of the target object passes through the glass of the mirror, there will be a refractive offset (error) between the two images due to the thickness of the glass.

Figure 11:
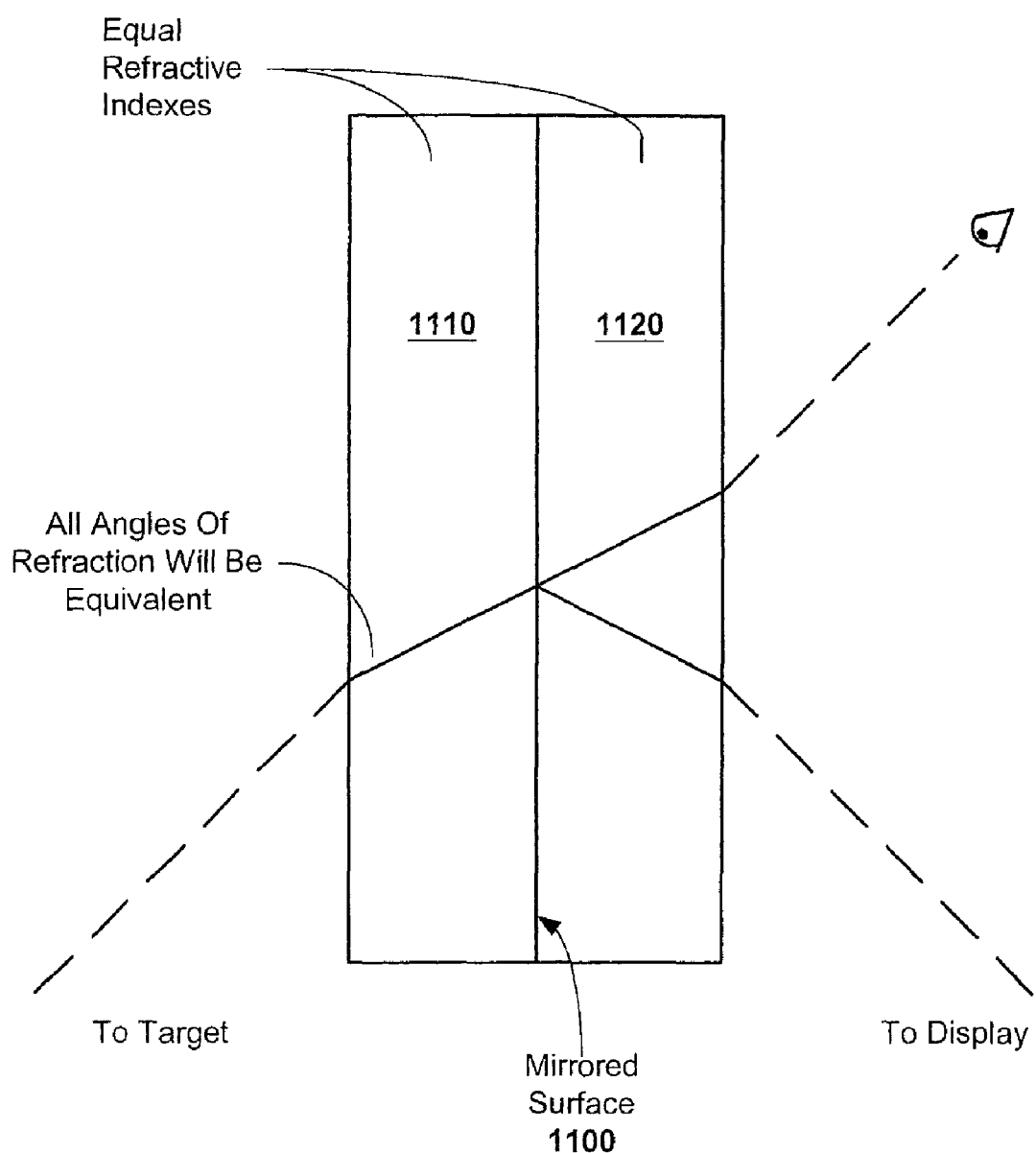
FIG. 11 details a reflective surface embedded between two surfaces with equivalent refractive properties.

FIG. 11 shows one exemplary apparatus for addressing this potential limitation. In FIG. 11, a cross-section of the mirrored surface 1100 of the half-silvered mirror is shown between two equal thickness pieces of glass 1110, 1120 (with the same refractive index). With this structure, both the direct view and the reflected image will pass through the glass 1110, 1120 and be refracted an equivalent amount. In other words, the same error due to refraction will be imparted to each of the image lines. This orientation will therefore preferably correct for the problems of refraction in the half-silvered mirror.

Figure 12:
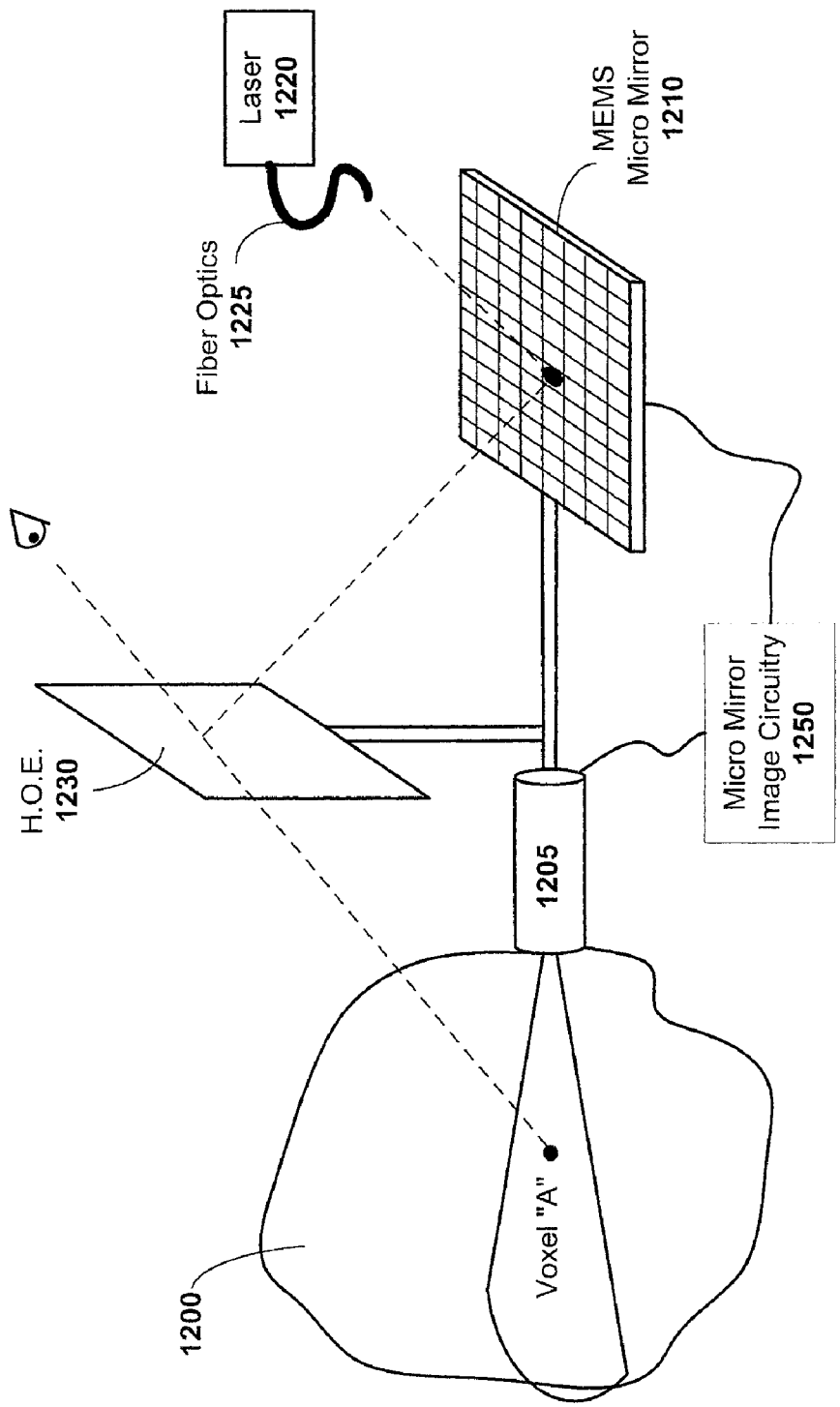
FIG. 12 shows an embodiment of the present invention with a holographic plate.

The half-silvered mirror embodiments of the present invention (described above) could also be altered to use a Holographic Optical Element (HOE) instead of the mirror. This is just another example of the generalized "partially reflective, partially transparent, surface." For example, FIG. 12 shows one presently preferred embodiment of the present invention including an ultrasound transducer 1205 with an HOE or "holographic plate" 1230 and a micro-mirror MEMS chip 1210 mounted thereon. An HOE 1230 is the hologram of an optical system that serves the same function normally performed by mirrors and lenses. The micro-mirror MEMS chip 1210 preferably contains a large array of individual micro-mirrors, for example in a grid pattern as shown in FIG. 12.

This system works by reflecting laser light 1220 off of each of the micro-mirrors that make up the micro-mirror device 1210. The captured tomographic slice image is used to control (via circuitry 1250) each of the tiny micro-mirrors 1210 to determine whether or not the laser light 1220 is reflected up the HOE 1230. Specifically, the output of a laser 1220 may be routed via a fiber optic cable 1225 to the micro-mirror chip 1210 so that coherent light may be reflected onto the HOE 1230 by any given micro-mirror when that particular micro-mirror is activated. This activation is determined by a given pixel in a video signal from the ultrasound transducer which represents a voxel (A) in the ultrasound slice.

The video image from the image capture device 1205 (e.g., ultrasound scanner) may be appropriately scaled, rotated, translated and cropped (via circuitry 1250) to occupy the array of micro-mirrors on the chip 1210. The HOE 1230 is preferably designed so that light reflected by a given micro-mirror appears to emanate from a particular location within the target, namely, the location of the voxel (A) in the tomographic scan corresponding to that particular pixel in the ultrasound image. Thus, the ultrasound slice as a whole appears to emanate in real-time from within the target object 1200 at its actual location.

Although FIG. 12 shows the major components of such a holographic system, parts of the optical system (mirrors and/or lenses) required to direct the laser light 1220 onto the micro-mirror chip 1210 and the phase modulation system used to reduce speckle normally resulting from coherent light are not shown for clarity. These and other desired components of a laser light system are well known to one skilled in the art. Additionally, FIG. 12 depicts only the particular case involving an ultrasound scanner capturing a single tomographic slice. Other tomographic imaging modalities, including those that operate in 3D (described above), may also be displayed using this method, since the 2D array of micro-mirrors can be mapped into a 3D space within the patient.

The holographic system establishes the geometric relationship between the micro-mirrors and the virtual tomographic image. The content of the image is established by the video signal from the ultrasound scanner, whose pixels control to the individual elements of the micro-mirror device. It is further noted that the HOE embodies a transform function for creating a magnified view-independent virtual image that could be created using lenses and mirrors, whereas non holographic optical elements would be very large and somewhat less desirable.

Figure 13:
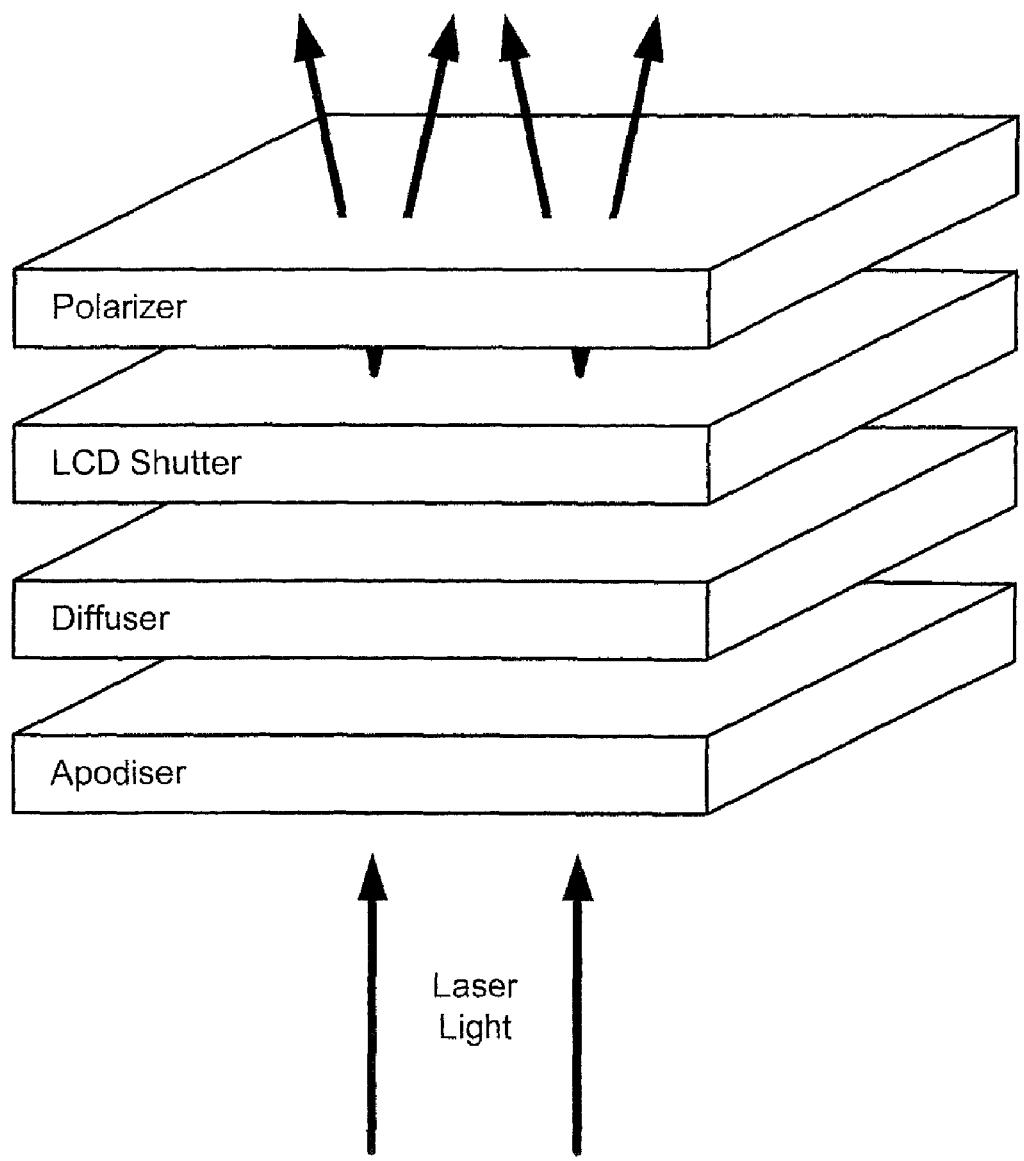
FIG. 13 shows exemplary material layers combined in an LCD.

Difficulties may arise with the use of the micro-mirror device due to the small angle of deflection capable in the micro-mirrors. Therefore, other devices could be used in place of the MEMS device such as a Liquid Crystal Display (LCD) or any device capable of switching on/off individual localized sources of monochromatic light directed at the HOE 1230. For example, FIG. 13 shows an exemplary LCD shutter with laser light (attempting) to pass through the shutter towards the HOE. In FIG. 13, the directional laser light passes through the non-polarizing apodiser and diffuser. The LCD shutter and the polarization layer work in tandem to determine the amount of light that passes through each LCD shutter based on the relative polarization of these two layers.

Each LCD shutter can be quickly turned on/off so as to direct the ultrasound image up to the HOE. In much the same was as with the MEMS device, each individual LCD shutter may correspond to a pixel in the captured tomographic slice and will be turned on/off based on whether that pixel currently exists in the image. With sufficiently fast switching, the same result on the face of the HOE is achieved.

Figure 14A:
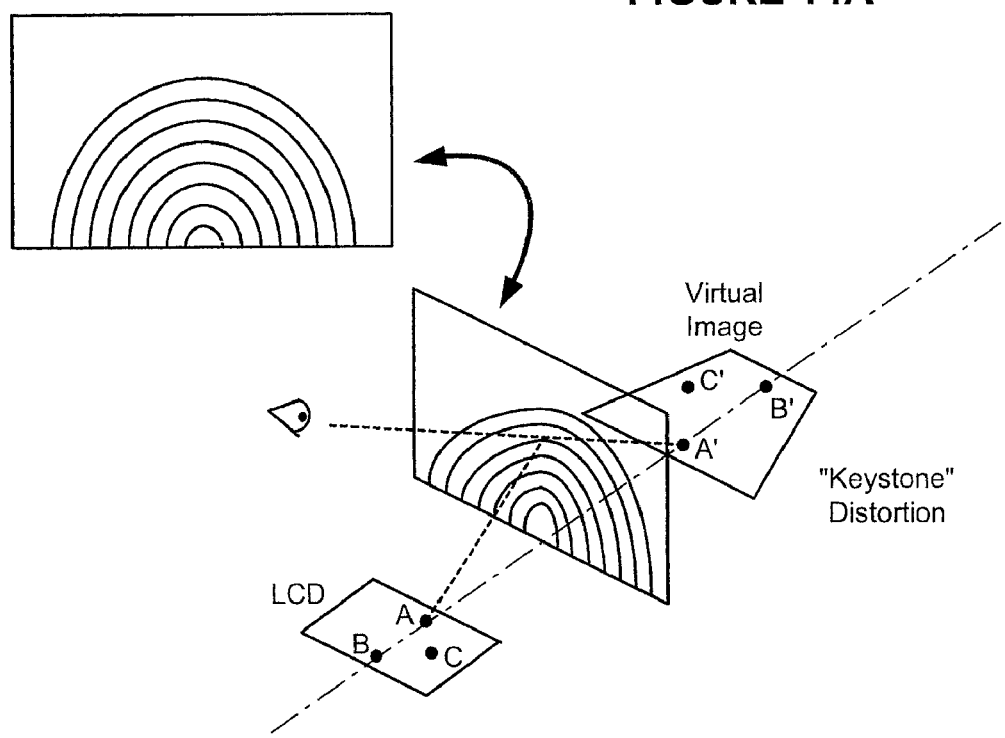
FIG. 14 shows an embodiment of the present invention utilizing interference principles.

A simplified version of the HOE could also be used in the present invention as depicted in FIG. 14. For example, it is known in general optics that the hologram of an ideal mirror is simply a grating. The hologram of a simple convex lens is a zone-plate, i.e., a series of concentric rings that create an interference pattern.

The hologram pattern can be calculated using the lens equation: $1/x+1/y=1/f$ (where x=distance from lens on one side; y=distance from lens on the other side; and f=focal length). A series of correspondence points thus exists on opposite sides of the lens which can be used to project the array of emission points (from the MEMS micro mirrors or LCD device) to the corresponding virtual locations in the ultrasound slice. In other words, a single hologram can map the whole image, rather than a separate hologram for each pixel. The same approach could be used to map from the MEMS (or LCD) device mounted parallel to the HOE to a "C-mode" slice from a 3D ultrasound machine, as described earlier and shown in FIG. 3.

Figure 14B:
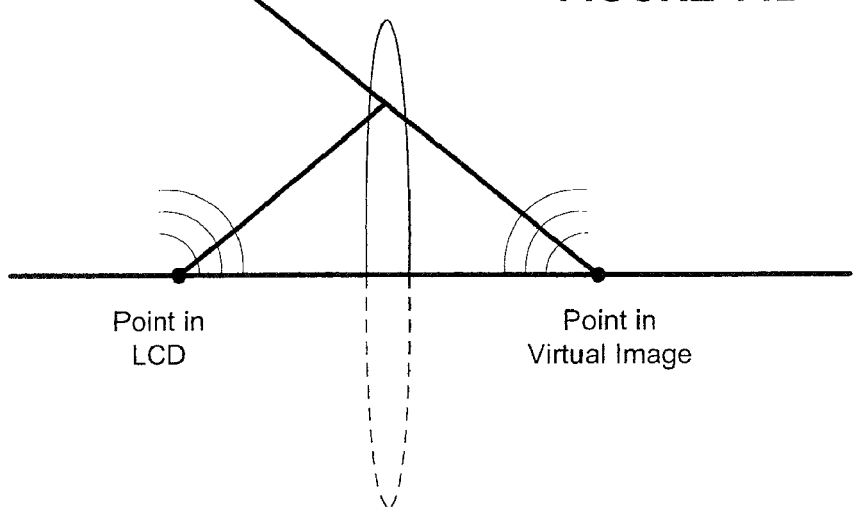

The hologram of a tomographic slice, therefore, would generally be an off-axis sector of this zone plate as shown in FIG. 14. The partial spherical etches in the HOE will produce spherical wavefronts from A', B', C' when illuminated at A, B, C with coherent light, because the zone plate acts as a lens. FIG. 14B shows a side view of the device. However, the hologram will have some "keystone-shaped" distortions as shown in FIG. 14. These distortions can be compensated for by a corresponding distortion of the image sent to the MEMS or LCD device (from circuitry 1250). There may also be problems with resolution in parts of the image due to inefficient use of the entire MEMS or LCD device. The 3D ultrasound version might also experience distortion or curvature in the "C-mode" slice, and these may be corrected by judicious selection of the particular voxels to be displayed.

The resulting HOE is a much simpler 2D HOE that could be implemented as a "surface plate" rather than the HOE described above that would likely require a "volume plate". The surface plate is easier to manufacture and may be much cheaper to produce. The present HOE may be manufactured by etching the calculated pattern into a chromium-coated glass plate.

The present invention may also be used to display multiple tomographic slices simultaneously. For example, this can be accomplished using the mirror orientation described in several embodiments above with the addition of multiple flat panel displays. If each of the flat panel displays was oriented with respect to the viewer-side face of the half-silvered mirror (according to the calibration methodologies described above), then multiple tomographic slices could be superimposed on the direct view of the target object on the face of the half-silvered mirror. This may give the impression of seeing an internal 3D view of the target object. However, because all of the various images are reflected to a flat surface, the resulting combined image may be difficult to comprehend in certain circumstances.

Alternatively, multiple MEMS micro-mirror devices or multiple LCD shutters could be used to simultaneously display multiple captured slice images in real-time on the HOE. In the same way as multiple flat panel displays may be used with the half-silvered mirror embodiments, two or more micro-mirror devices or LCD shutters could be oriented such that they direct laser light to the HOE to simultaneously show multiple tomographic slice images on the HOE. Alternatively, by dividing a single MEMS into several sections, each with a different holographic transform, multiple slices could appear to be displayed on the HOE simultaneously. However, crosstalk between the slices may be easier to minimize if each image is displayed on its own MEMS chip, rather than sharing sections of a single MEMS chip. The HOE device also has the advantage over the mirror that a slice displayed roughly "edge-on" could be viewed from either side by moving the viewpoint. This multiple-device orientation may reduce alignment problems related to showing multiple slices on one device, but it may also increase the cost of the system. Therefore, different orientations of these components will be preferred for different applications.

Clip-On Mirror Embodiments

In many uses of the present invention, it is preferred to keep the portions of the device that are in contact with the patient in a sterilized condition. However, since the present invention preferably employs clear optical paths, utilizing some type of enclosure around the entire device to maintain a sterile environment is impractical, in particular those parts involved with the optical paths. To address this situation, an optional embodiment of the present invention utilizes a removable "clip-on" mirror with the teachings of the above invention in order to provide a sterile environment as described below.

Specifically, when using an image capture device, such as an ultrasound scanner, the device typically needs to be sterile. In most applications, this is accomplished by covering the image capture device with a disposable bag that has been sterilized and is only used for a single procedure. While such a covering works well with traditional ultrasound (in which the operator views the image on a separate monitor away from the patient), such a covering is impractical when using the present invention. For example, a bag or other covering over the partially-silvered mirror or display will degrade the image seen by the operator (through the mirror) and may cause the system to function at a less than optimal level.

Figure 15:
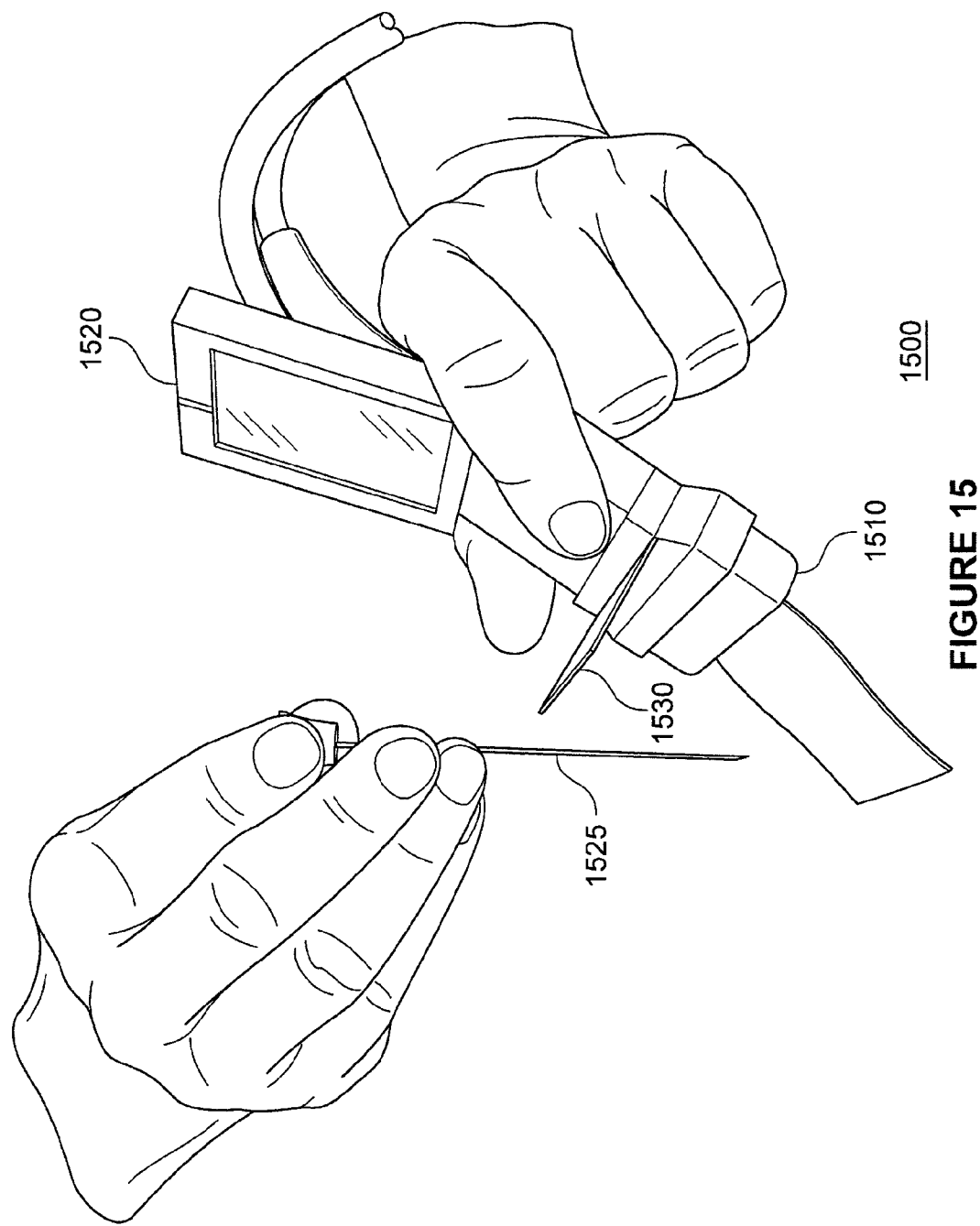
FIG. 15 shows an exemplary imaging device.

FIG. 15 shows one embodiment of an imaging device 1500 according to the present invention. As described in detail above, the device 1500 generally comprises an image capture device 1510 and a display 1520 which displays the captured data in two dimensions. A half-silvered mirror 1530 or other partially reflective surface is positioned between the image capture device 1510 and the display 1520 such that a reflected version of the displayed image is merged with a direct view of the operator's line-of-sight on the front surface (nearest the display) of the mirror 1530. As described above, this system facilitates the viewpoint-independent merging of the captured tomographic image of internal features of the target object (e.g., a patient) with the operator's direct view of the external features of the object. FIG. 15 shows the device 1500 being used to guide needle 1525 insertion.

Figure 16C:
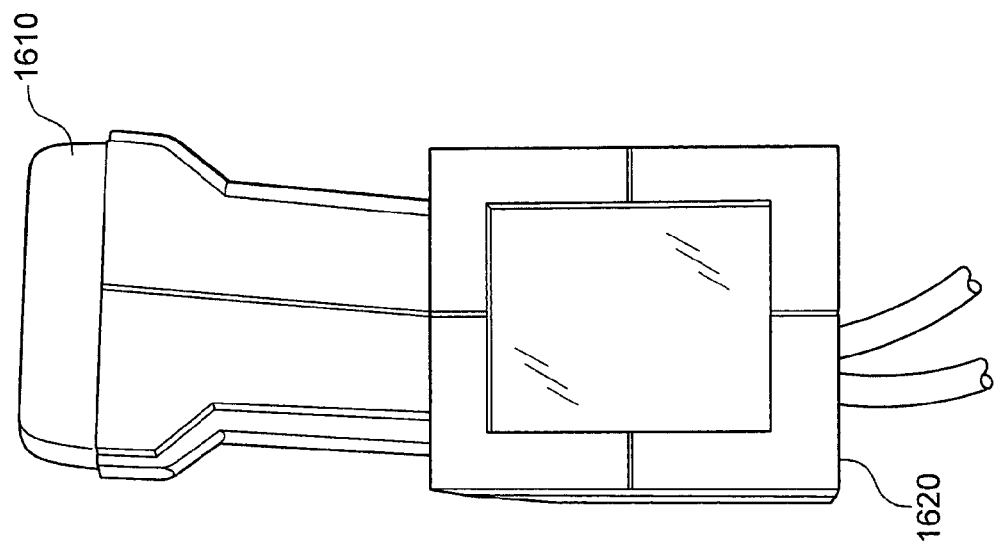
FIG. 16 shows the component parts of an exemplary sterile imaging device including the image capture device and display (FIG. 16C), the half-silvered mirror and mirror housing (FIG. 16B) and an optional hood (FIG. 16A)
Figure 16B:
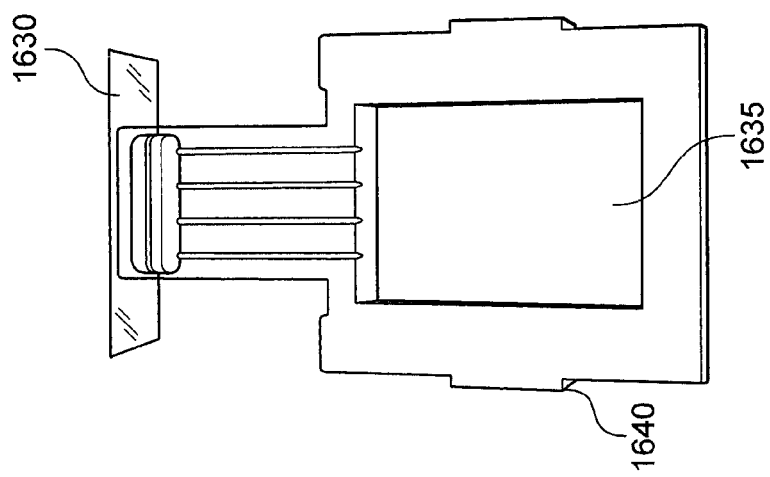

Sterilizing the device 1500 of FIG. 15 by the conventional "bag" method would degrade the optical performance of the system. Therefore, to address this limitation in sterile environments, an optional embodiment of the present invention uses a disposable half-silvered mirror that is separate from a sterile image capture device/monitor unit. Specifically, FIG. 16 shows one example of the component parts of this optional embodiment. FIG. 16C generally shows the image capture device and display; FIG. 16B shows the half-silvered mirror and clip-on housing to attach to the image capture device and display over the disposable bag; and FIG. 16A shows an optional hood.

In more detail, FIG. 16C shows the main portion of the imaging device from FIG. 15. Specifically, an image capture device 1610 and display 1620 are shown connected to a central housing in an identical relationship to each other as defined by the previous embodiments. This display 1620 and image capture device 1610 may be easily inserted into a conventional sterile "bag" as is common in ultrasound and other imaging methodologies. Note that this structure is separated from the half-silvered mirror that is incorporated into the structure in several prior embodiments.

FIG. 16B shows the half-silvered mirror 1630 for use with the structure of FIG. 16C. The mirror 1630 is securely attached to a frame 1640 that is adapted to be "snapped" or otherwise easily attached to the structure of FIG. 16C. Preferably, the mirror housing 1640 is so adapted to securely (and removably) attach to the image capture device/display structure in FIG. 16C securely at the proper location and orientation. The mirror housing 1640 also preferably includes an open area 1635 that allows the image from the display (1620) to be transmitted up to the half-silvered mirror 1630 when the housing 1640 is in place on the structure of FIG. 16C. This open area 1635 may include a piece of optical glass, plastic or may just represent a hole in the housing 1640. In either case, it may effect a flattening of the bag directly over the display, further reducing distortion from the bag. The housing 1640 and the half-silvered mirror 1630 are designed such that the optical paths described above hold true when the housing 1640 is snapped into place on the structure of FIG. 16C.

Figure 16A:
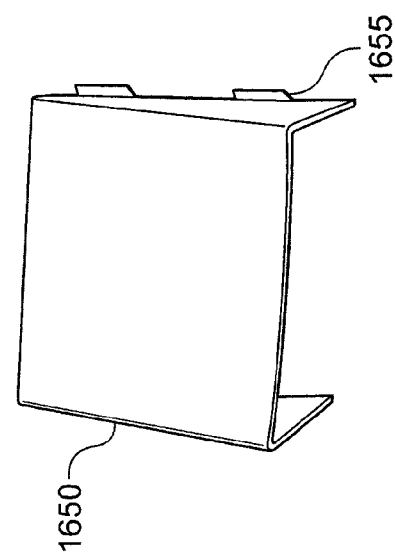

FIG. 16A shows an optional housing 1650 that may be snapped into place on the mirror housing 1640 shown in FIG. 16B. This additional housing preferably reduces outside glare or the intrusion of light from outside sources in the hospital room or environment. The housing 1650 may include a tab or other protrusion 1655 that allows the housing to easily and securely mate with the mirror housing 1640 described above.

Figure 17:
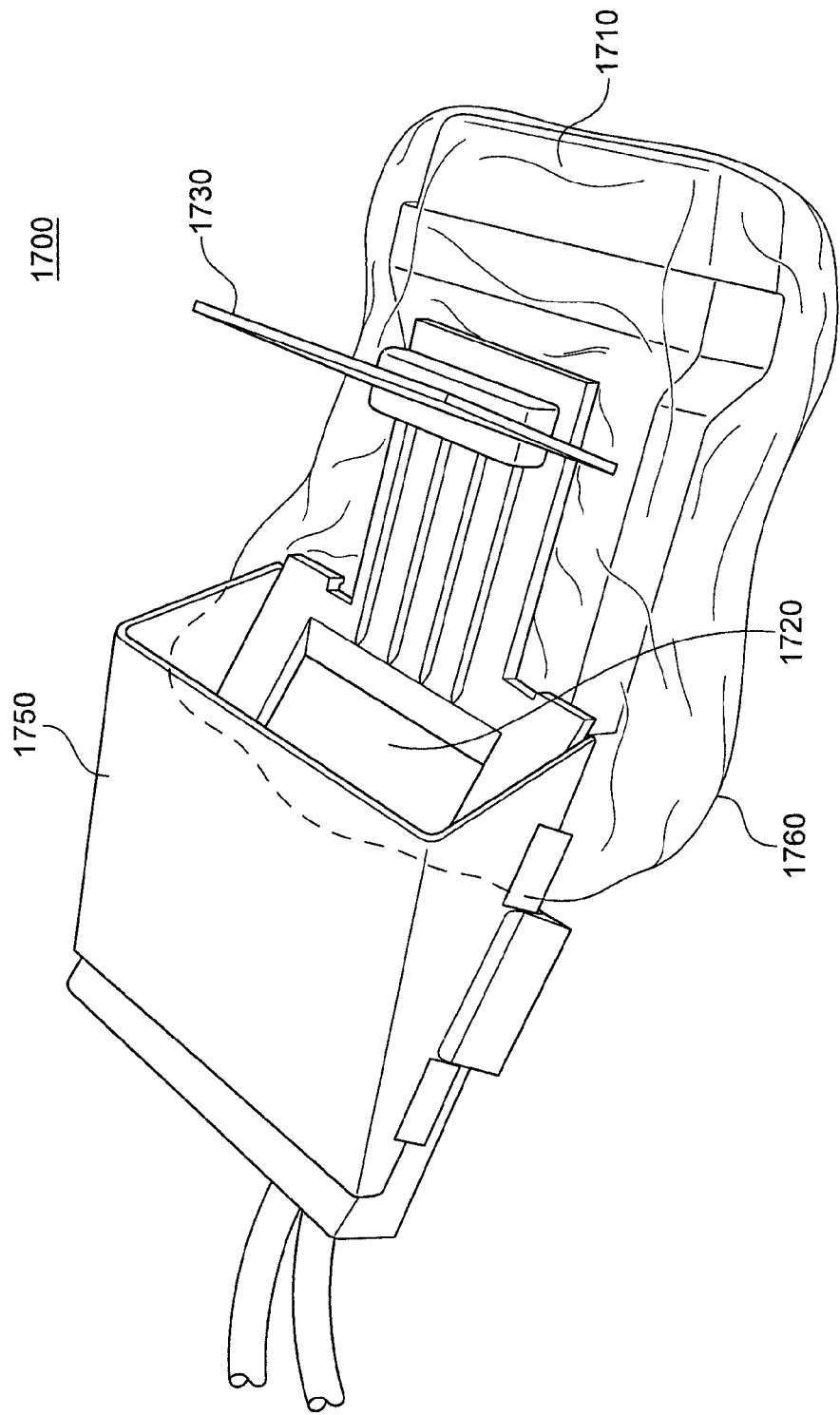
FIG. 17 shows an exemplary sterile imaging device as assembled.

FIG. 17 shows the sterile version of the imaging device 1700 of the present invention after all of the above-described components have been assembled. Specifically, the image capture device 1710 and display 1720 are shown inside a sterile plastic bag 1760 according to standard imaging practices. The portion of the bag 1760 that covers the face of the display 1720 has been stretched taut and the mirror housing has been snapped into place over the display 1720 and bag 1760. By stretching the bag taut, this process limits the distortion that the bag creates in the image that is reflected from the display 1720 up to the half-silvered mirror 1730 (which is outside of the bag 1760). Note that hood 1750 has been snapped into place over the display in order to limit the amount of ambient light that interferes with the reflection of the captured image from the display 1720 up to the partial mirror 1730.

In the device 1700 of FIG. 17, the operator's direct line-of-sight of a target object through the half-silvered mirror 1730 is completely unobscured by the bag. Moreover, the image reflected on the face of the partial mirror 1730 travels only through a single, taut layer of thin plastic on its way from the display 1720 up to the mirror. In this way, there is a minimum amount of distortion of the combined (tomographic and direct) image streams while maintaining the sterile nature of the imaging system 1700.

At the end of a procedure, the mirror housing (with attached mirror) can be discarded and a new mirror housing/mirror can be utilized for the next procedure. By using a new sterile bag (1760) around the image capture device and display, and by utilizing new sterile versions of the remaining disposable parts of the device, a sterile imaging system is employed.

One skilled in the art will appreciate many alternatives of this sterile embodiment according to the present invention within the scope of the present teachings. In some embodiments, the mirror/housing of FIG. 16B may simply be adapted to be sterilized rather than being disposable. For example, the assembly could be coated with a material that would allow the assembly to be submerged in a sterilizing fluid such as alcohol or allow the assembly to autoclaved, thereby reducing the costs of sterilization. One of skill in the art would recognize numerous coatings that would be permissive of submersion in a sterilizing fluid. Moreover, the attachment between the mirror/housing and the structure of FIG. 16C could take many forms including: pegs with mated holes; tabs with mated slots; removable adhesive or magnetic connectors with guiding pegs/slots and similar attachment mechanisms. The mirror/housing and the display could be incorporated into a single structure (which can be attached to the image capture device only) if the mirror/housing and display were completely sealed such that together they created a sterile environment when inserted over the structure of FIG. 16C. Finally, the mirror/housing and the bag could be incorporated into a single structure, simplifying attachment and possibly improving the optics of the plastic over the display. Moreover, colored indicators or markers could be employed on all attachable structures to aid a user in assembling the device in an almost effortless manner.

Although the invention has been described in terms of particular embodiments in an application, one of ordinary skill in the art, in light of the teachings herein, can generate additional embodiments and modifications without departing from the spirit of, or exceeding the scope of, the claimed invention. Accordingly, it is understood that the drawings and the descriptions herein are proffered only to facilitate comprehension of the invention and should not be construed to limit the scope thereof.

What is claimed is:

1. An imaging device comprised of:
   an image capture device for capturing an image of the internal structure of a target object;
   a display for displaying a captured image from the image capture device; and
   a partially reflective surface oriented to reflect the captured image to an operator of the imaging device, such that the reflected captured image forms a virtual image that is geometrically superimposed with said internal structure being imaged and is merged with a direct view of the target object independent of the viewing location of the operator when the angle between the surface and the display is equal to the angle between the surface and an image plane, wherein the image capture device and display are enclosed in a sterile container.

2. The imaging device of claim 1, wherein the sterile container is a probe bag.

3. The imaging device of claim 1, wherein the partially reflective surface is incorporated into a mirror housing.

4. The imaging device of claim 3, wherein said mirror housing is removably attached to said display and image capture device.

5. The imaging device of claim 3, wherein said mirror housing includes an aperture adapted to cover said display.

6. The imaging device of claim 5, wherein said aperture comprises optical glass or clear plastic.

7. The imaging device of claim 1, wherein said image capture device, said display and said partially reflective surface are all coated so that they may be submersed in a sterilizing fluid without losing any reflective material from said partially reflective surface.

8. The imaging device of claim 1, wherein said image capture device captures a two-dimensional image.

9. The imaging device of claim 8, wherein said two-dimensional image is an ultrasound image.

10. The imaging device of claim 1, wherein said image capture device captures a three-dimensional image.

* * * * *